(12) United States Patent
Cho et al.

(10) Patent No.: US 9,863,951 B2
(45) Date of Patent: Jan. 9, 2018

(54) RARE CELL ISOLATION DEVICE, RARE CELL ISOLATION METHOD, AND RARE CELL DETECTION METHOD USING THE SAME

(71) Applicant: UNIST ACADEMY-INDUSTRY RESEARCH CORPORATION, Ulsan (KR)

(72) Inventors: Yoon Kyoung Cho, Ulsan (KR); Young Lim Lee, Daegu (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 32 days.

(21) Appl. No.: 14/494,764

(22) Filed: Sep. 24, 2014

(65) Prior Publication Data

US 2015/0314290 A1 Nov. 5, 2015

(30) Foreign Application Priority Data

Apr. 30, 2014 (KR) .......................... 10-2014-0052538

(51) Int. Cl.
*G01N 1/40* (2006.01)
*G01N 33/574* (2006.01)
(Continued)

(52) U.S. Cl.
CPC .......... *G01N 33/574* (2013.01); *B01D 61/18* (2013.01); *B01D 63/087* (2013.01); *B01D 63/16* (2013.01); *B01L 3/50273* (2013.01); *B01L 3/502753* (2013.01); *C12Q 1/6886* (2013.01); *G01N 1/4005* (2013.01); *G01N 15/0227* (2013.01);
(Continued)

(58) Field of Classification Search
None
See application file for complete search history.

(56) References Cited

U.S. PATENT DOCUMENTS

2008/0056949 A1* 3/2008 Lee ..................... B01L 3/50273
422/72
2009/0176899 A1* 7/2009 Yoo .................. B01L 3/502707
521/50.5
(Continued)

FOREIGN PATENT DOCUMENTS

KR 10-2013-0080307 7/2013
KR 10-2015-0045816 4/2015

OTHER PUBLICATIONS

Lee et al. A fully automated immunoassay from whole blood on disc. Mar. 6, 2009. The Royal Society of Chemistry. vol. 9, pp. 1548-1555.*

(Continued)

*Primary Examiner* — Channing S Mahatan
(74) *Attorney, Agent, or Firm* — Lex IP Meister, PLLC

(57) ABSTRACT

The present invention provides a rare cell isolation device including: a first body which is disposed above a filtration membrane and includes a first inlet for injecting a biospecimen; and a second body which is disposed under the first body and bonded to the filtration membrane, wherein the first body and the second body have a disk-shaped structure to be rotatable around their centers, and the filtration membrane is disposed to be separated from the center of the second body in a radial direction.

17 Claims, 23 Drawing Sheets
(2 of 23 Drawing Sheet(s) Filed in Color)

(51) Int. Cl.
 B01L 3/00 (2006.01)
 C12Q 1/68 (2006.01)
 G01N 15/02 (2006.01)
 B01D 61/18 (2006.01)
 B01D 63/08 (2006.01)
 B01D 63/16 (2006.01)
 G01N 15/00 (2006.01)
 G01N 1/31 (2006.01)
 C12M 1/00 (2006.01)

(52) U.S. Cl.
 CPC ... *G01N 15/0272* (2013.01); *G01N 33/57492* (2013.01); *B01D 2315/02* (2013.01); *B01L 2200/0652* (2013.01); *B01L 2200/10* (2013.01); *B01L 2300/0681* (2013.01); *B01L 2300/0803* (2013.01); *B01L 2300/0864* (2013.01); *B01L 2300/0887* (2013.01); *B01L 2400/0409* (2013.01); *C12M 47/04* (2013.01); *C12Q 1/6806* (2013.01); *G01N 1/31* (2013.01); *G01N 2001/4088* (2013.01); *G01N 2015/0065* (2013.01)

(56) References Cited

U.S. PATENT DOCUMENTS

2010/0028915 A1* 2/2010 Gualberto .......... G01N 33/5023 435/7.23
2012/0024083 A1* 2/2012 Wo .................... B01L 3/502738 73/863.21
2013/0209988 A1* 8/2013 Barber ............. B01L 3/502753 435/5
2014/0008210 A1* 1/2014 Guia ...................... G01N 1/34 204/158.21

OTHER PUBLICATIONS

Templeton et al. A novel filtration method integrated on centrifugal microfluidic devices. Published online: Nov. 24, 2013. Microfluid Nanofluid. vol. 17, pp. 245-251.*

Office Action, Korea Patent Office, Application No. 10-2014-0052538, dated Oct. 27, 2015 6pages.

Jong-Myeon Park et al., "Fully Automated Circulating Tumor Cell Isolation Platform with Large-Volume Capacity Based on Lab-on-a-Disc", Analytical Chemistry, vol. 86, pp. 3735-3742, Mar. 18, 2014.

Jian Chen et al., "Microfluidic approaches for cancer cell detection, characterization, and separation", Lab on a Chip, vol. 12, Issue 10, pp. 1753-1767, Apr. 24, 2012.

* cited by examiner

RARE CELL ISOLATION DEVICE, RARE CELL ISOLATION METHOD, AND RARE CELL DETECTION METHOD USING THE SAME

CROSS-REFERENCE TO RELATED APPLICATION

This application claims priority to and the benefit of Korean Patent Application No. 10-2014-0052538 filed in the Korean Intellectual Property Office on Apr. 30, 2014, the entire contents of which are incorporated herein by reference.

BACKGROUND OF THE INVENTION

(a) Field of the Invention

The present invention relates to a rare cell isolation device, a rare cell isolation method, and a rare cell detection method using the same.

(b) Description of the Related Art

Within body fluid, particularly blood, of a patient with a disease, there are various bio-particles including a cell that can serve as an index of the disease as well as blood cells such as red blood cells, white blood cells, platelets, and the like.

Among them, representatively, there is a circulating tumor cell (CTC) as a tumor cell distributed in blood of a metastatic cancer patient. The CTC is a cell detached from a primary tumor cell and circulating in the bloodstream, and it penetrates into other tissues and causes metastasis of cancer. Such a circulating tumor cell is a bio-particle that is highly useful as a tumor marker in a cancer diagnosis and treatment field since it is a causative factor of occurrence and growth of metastatic cancer and can provide a variety of information relevant to staging of cancer in a patient.

That is, it is known that the number of circulating tumor cells present in blood of a patient is closely related to a progression stage of cancer. Therefore, capturing them and counting the number thereof is very useful in understanding staging of tumors and observing prognosis of cancer treatment. Also, a specific treatment method can be applied depending on the number of circulating tumor cells, and thus, it is greatly helpful in designing a direct treatment method. Further, through DNA/RNA molecular diagnosis, it is possible to obtain genetic information of target cancer cells. A cancer diagnosis based on this can provide a patient-specific treatment to each patient, and thus, enables more efficient treatment of cancer.

Meanwhile, as compared with a blood cell, a circulating tumor cell is very rare with a ratio of one circulating tumor cell to one hundred million blood cells. Therefore, in order to use a circulating tumor cell detection result as a marker to determine a progression stage of cancer or malignancy of a cancer cell, a very delicate and precise cell isolation technique is demanded.

Until now, the CellSearch® system manufactured by Johnson & Johnson has been the only product approved by the United States Food and Drug Administration (FDA) as a circulating tumor cell detector practically used in a cancer diagnostic assay. Many groups have already conducted various clinical tests using the CellSearch® system, and reliability of detection results has been proven to some extent. The CellSearch® system performs a pre-treatment process of removing red blood cells based on a difference in cell density between cancer cells and blood cells prior to a substantive capturing process. Then, a specimen is added and reacts with magnetic particles coated with the EpCAM (Epithelial Cell Adhesion Molecule) antibody which is specifically bonded to a cancer cell, so that a cancer cell is specifically isolated and a result thereof is detected by the immunofluorescence method.

Furthermore, many groups have already developed various microchip-based circulating tumor cell detection platforms. Like the Cellsearch® system, many detection techniques isolate a cancer cell by making an antibody react with a cancer-specificantigen, that is, EpCAM, which is expressed specifically in almost all cancer cells. However, such a cancer cell capturing technique based on a biochemical method has a capture efficiency which varies depending on an EpCAM expression level of a target cancer cell, and thus it is limited in capturing various kinds of cancer cells having different EpCAM expression levels with high sensitivity.

In order to overcome the above-mentioned limitation, many cases have been suggested where an isolation method is suitable for a physical property of a cell is grafted onto a microchip. For example, a representative background art reference relating to a technique of capturing and detecting a cell based on a difference in size between a cancer cell and a blood cell is Korean Patent Laid-Open Publication No. 10-2012-0117834, which, to be specific, discloses a filtering system including a filtering module for isolating a target bio-particle or cell, and a cell filtering method using the filtering system.

However, the above-described conventional microchip-based cancer cell capturing devices have many drawbacks. The conventional cancer cell capturing devices use whole blood diluted for prevention of blood coagulation, or performs a separate filtering process of isolating and removing blood cells from whole blood prior to a substantive capturing process. During such a pre-treatment process, a loss of target cancer cells occurs. Further, a dead volume occurring at a connecting portion of the microchip such as tubing, a connector, and the like, may cause a loss of target cancer cells.

Furthermore, due to the characteristics of the microchip, a specimen storage unit and a micro-flow path constituting a device have a very small size in the unit of several micrometers (μm). Thus, it takes a long time of several hours or more to complete a process of isolating target cancer cells.

Therefore, if a size-based cancer cell isolation device requiring a relatively short time of about several tens of minutes for cancer cell isolation is used, a micro-filter membrane used in an isolation process needs to be disassembled from the device for result analysis.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a rare cell isolation device capable of minimizing a loss of target cancer cells during a specimen filtering process and reducing time required for target cell isolation, a rare cell isolation method capable of isolating a rare cell from a specimen without disassembling some constituent elements within the isolation device, and a rare cell detection method capable of promptly detecting and analyzing the isolated rare cell within the rare cell isolation device.

An exemplary embodiment of the present invention provides a rare cell isolation device including: a filtration membrane which filters a biospecimen; a first body which is disposed above the filtration membrane and includes a first inlet for injecting the biospecimen; and a second body which is disposed under the first body and bonded to the filtration membrane, wherein the first body and the second body have a disk-shaped structure to be rotatable around their centers, and the filtration membrane is disposed to be separated from the center of the second body in a radial direction.

The rare cell isolation device may further include a filtrate storage unit which is formed at a contact portion between the first body and the second body and is connected to the filtration membrane.

The first body may include: an upper plate through which the first inlet penetrates; and a first intermediate plate which is coupled to a lower part of the upper plate, on its one side.

The first body may include a first guiding unit which is formed at a contact portion between the upper plate and the first intermediate plate and of which one side is connected to the first inlet and the other side is connected to the filtration membrane.

The upper plate may include a ventilation hole which is connected to the first guiding unit.

The second body may include: a second intermediate plate that is bonded to the filtration membrane; and a lower plate which is coupled to a lower part of the second intermediate plate.

The second intermediate plate or the lower plate may include a first flow path which connects the filtration membrane and the filtrate storage unit.

The first inlet may be disposed between the center of the first body and the filtration membrane.

The first guiding unit may include: a first portion which penetrates through the first intermediate plate and gradually increases in width in a radial direction of the first body based the center of the first body; and a second portion which penetrates through the first intermediate plate and gradually decreases in width in the radial direction of the first body from an end of the first portion based on the center of the first body.

The second intermediate plate may include a penetrating portion formed at a contact portion with the first guiding unit.

The penetrating portion may include: a first hole which is formed in a circular shape at the second intermediate plate; and a second hole which is formed at a lower part of the second intermediate plate and formed in a concentric circular shape having a greater exterior diameter than the first hole.

The filtration membrane may penetrate through a lower side of the second hole and may be bonded to the lower part of the second intermediate plate.

There may be multiple first guiding units formed in a radial direction based on a central portion of the body.

The first body may include: a second inlet which penetrates through the upper plate and is disposed on a central side of the first body; and a second guiding unit which is formed at a contact portion between the upper plate and the first intermediate plate and of which one side is connected to the second inlet and the other side is connected to the second portion.

There may be multiple second inlets and second guiding units disposed in a radial direction based on the center of the first body.

A detection solution storage unit connected to the filtration membrane may be formed at the contact portion between the first body and the second body, and a second flow path which is branched from the first flow path between the second intermediate plate and the lower plate and connecting the first filtration membrane and the detection solution storage unit is formed.

A reversible valve may be provided in the first flow path, the second flow path, or at least one of third flow paths which connect the first guiding unit and the second guiding unit to adjust a flow rate flowing into the filtration membrane and a flow rate discharged from the filtration membrane.

Another exemplary embodiment of the present invention provides a rare cell isolation method using the rare cell isolation device, including: injecting the biospecimen into the rare cell isolation device; guiding the biospecimen to the filtration membrane by generating centrifugal force; and filtering the biospecimen through the filtering filtration membrane.

Yet another exemplary embodiment of the present invention provides a rare cell detection method using the rare cell isolation device, including: injecting the biospecimen into the rare cell isolation device; guiding the biospecimen to the filtration membrane by generating centrifugal force; filtering the biospecimen through the filtration membrane; washing the rare cell isolated on the filtration membrane; staining the rare cell; and detecting the stained rare cell.

The step of staining may include injecting a staining reagent into the second guiding unit and staining the rare cell isolated on the filtration membrane.

The step of detecting may include detecting the stained rare cell using an optical microscope.

Still another exemplary embodiment of the present invention provides a rare cell detection method for detecting a rare cell isolated by the rare cell isolation method, including: injecting the biospecimen into the rare cell isolation device; guiding the biospecimen to the filtration membrane by generating centrifugal force; filtering the biospecimen through the filtration membrane; washing the rare cell isolated on the filtration membrane; lysing the rare cell; and specifically amplifying a gene of the lysed rare cell.

The step of cell lysis may include injecting a a cell lysis solution into the second guiding unit and lysing the rare cell.

The rare cell isolation device according to an exemplary embodiment of the present invention can directly inject a biospecimen into a body without a separate pre-treatment, and thus a loss of rare cells in the biospecimen which occurs during a pre-treatment process can be minimized.

The rare cell isolation device according to an exemplary embodiment of the present invention can be rotated around the center, and thus a time required for filtering a biospecimen can be reduced using centrifugal force.

Further, the rare cell isolation device according to an exemplary embodiment of the present invention can directly stain a rare cell in a body or lyse the rare cell to be produced in the form of a detection solution, and thus the rare cell isolation device has a merit in that it can detect the rare cell without disassembling the body.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE EMBODIMENTS

Figure 1:
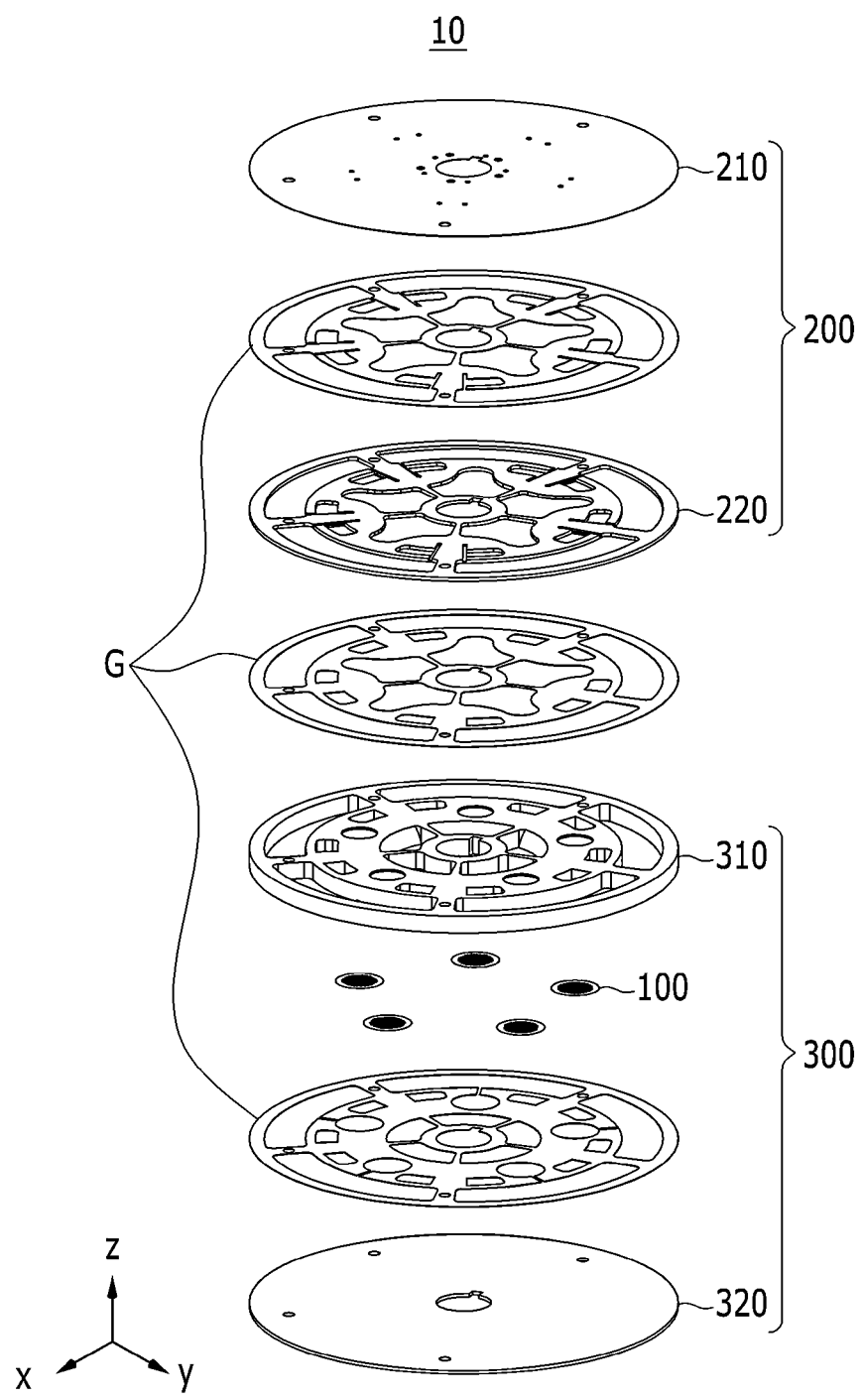
FIG. 1 is an exploded perspective view of a rare cell isolation device according to a first exemplary embodiment of the present invention.

Hereinafter, exemplary embodiments of the present invention will be explained in detail so that a person of ordinary skill in the art to which the present invention pertains can easily carry out the exemplary embodiments with reference to the accompanying drawings. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

Meanwhile, the term "on" as used in the present invention means that one element is disposed above or under a target element, but does not mean that one element is not necessarily disposed at an upper part based on the direction of gravity.

Further, through the whole specification, the term "comprises or includes" and/or "comprising or including" means that one or more other constituent elements, steps, and/or operations are not excluded in addition to the described constituent elements, steps, and/or operations unless context dictates otherwise. Furthermore, the sizes and thicknesses of the components illustrated in the drawings are approximately illustrated for convenience of explanation, and the present invention is not necessarily limited to the illustrations herein.

In the present invention, the term "biospecimen" includes all of fluids such as blood, saliva, urine, and the like, of a human body, an animal body, and a plant body. In the present invention, a whole blood specimen containing rare cells is used as a biospecimen and circulating tumor cells are used as the rare cells, but the present invention is not necessarily limited thereto.

FIG. 1 is an exploded perspective view of a rare cell isolation device according to a first exemplary embodiment of the present invention.

Referring to FIG. 1, a rare cell isolation device 10 according to the first exemplary embodiment of the present invention includes a filtration membrane 100 which can filter a biospecimen, a first body 200 which is disposed above the filtration membrane 100, and a second body 300 which is bonded to the filtration membrane 200 and coupled to a lower side of the first body 200.

In the filtration membrane 100 of the rare cell isolation device 10 according to the first exemplary embodiment of the present invention, micropores may be formed to have diameters in a range of 5 μm to 10 μm so that circulating tumor cells present in a whole blood specimen can be captured. However, this range includes an error which may occur when the filtration membrane 100 is bonded to the second body 300, and diameters of the micropores are not necessarily limited thereto and may vary depending on a size of a rare cell to be isolated.

Further, the filtration membrane 100 of the rare cell isolation device 10 according to the first exemplary embodiment of the present invention may be formed of a material which is biologically inactive and simultaneously has optical transmittance. Thus, it is possible to detect a rare cell with an optical detector without isolating the filtration membrane 100 from the second body 300.

Meanwhile, the filtration membrane 100 may be formed of the same material as the second body 300 so that it can be easily bonded to the second body 300. For example, if both of the second body 300 and the filtration membrane 100 are formed of a polycarbonate material, the filtration membrane 100 can be bonded to the second body 300 by injecting a small amount of acetone to an edge portion where the second body 300 is connected to the filtration membrane 100 and chemically dissolving a contact portion. Therefore, there is an effect of preventing leakage of rare cells caused by wrinkles or incomplete placement which may occur when the filtration membrane 100 is placed on the second body 300.

However, a method of bonding the filtration membrane 100 to the second body 300 of the rare cell isolation device 10 according to the first exemplary embodiment of the present invention is not necessarily limited to a chemical bonding method, and by various bonding methods such as thermal bonding, UV resin bonding, and ultrasonic bonding, the filtration membrane 100 can be non-reversibly bonded to the second body 300.

Meanwhile, referring to FIG. 1 again, the first body 200 and the second body 300 may have a disk-shaped structure to be rotatable around their centers. That is, the rare cell isolation device 10 according to the first exemplary embodiment of the present invention may have a disk structure in which the first body 200 and the second body 300 are sequentially stacked.

Herein, the filtration membrane 100 may be disposed to be separated from the center of the second body 300 in a radial direction.

The first body 200 and the second body 300 may be formed to have the same diameter as illustrated in FIG. 1.

Further, in the rare cell isolation device 10 according to the first exemplary embodiment of the present invention, a hollow space that simultaneously penetrates through the centers of the first body 200 and the second body 300 may be formed as illustrated in FIG. 1 so that a rotational shaft can be provided at a central portion.

Meanwhile, the rare cell isolation device 10 according to the first exemplary embodiment of the present invention may have a small disk structure in which the first body 200 and the second body 300 have a total height of 10 mm or less and the first body 200 and the second body 300 have diameters of 12 mm or less, but the present invention is not necessarily limited to such sizes.

In the rare cell isolation device 10 according to the first exemplary embodiment of the present invention, the first body 200 and the second body 300 may be formed of a material which is biologically inactive at a surface and simultaneously has optical transmittance, such as polystyrene, PS, polydimethylsiloxane (PDMS), polymethylmethacrylate (PMMA), polyacrylate, polycarbonate, polycyclic olefins, polyimide, polyurethanes, and the like.

Therefore, if a biospecimen is injected into the first body 200, the biospecimen does not react with the first body 200 and the second body 300, and thus the rare cell isolation device 10 has a merit in that biological stability can be obtained, and simultaneously, an optical detector can transmit the first body 200 and the second body 300 and detect the isolated rare cell without discharging the rare cell to the outside of the rare cell isolation device 10.

Referring to FIG. 1 again, the first body 200 of the rare cell isolation device 10 according to the first exemplary embodiment of the present invention may include an upper plate 210 including a first inlet 211 through which a biospecimen can be injected and a first intermediate plate 220 which is coupled to a lower part of the upper plate 210, on one side thereof, and the second body 300 may include a second intermediate plate 310 which is bonded to the filtration membrane 100 and a lower plate 320 which is coupled to a lower part of the second intermediate plate 310, on one side therefore.

As illustrated in FIG. 1, the rare cell isolation device 10 according to the first exemplary embodiment of the present invention may have a structure in which the upper plate 210, the first intermediate plate 220, the second intermediate plate 310, and the lower plate 320 are sequentially stacked. Herein, an adhesive layer G may be coated between the stacked plates. However, the rare cell isolation device 10 according to the first exemplary embodiment of the present invention is not necessarily limited to the structure in which these four plates are sequentially stacked or the adhesive layer G is coated on each layer as described above.

Meanwhile, referring to FIG. 1 again, a plurality of holes are formed in the upper plate 210, and a plurality of holes or protrusions and depressions are formed in the first intermediate plate 220 and the second intermediate plate 310. Thus, when the first intermediate plate 220 and the second intermediate plate 310 are coupled to the upper plate 210 and the lower plate 320, a space for storing the biospecimen and a flow path for transferring the biospecimen may be formed within the rare cell isolation device 10.

Figure 2:
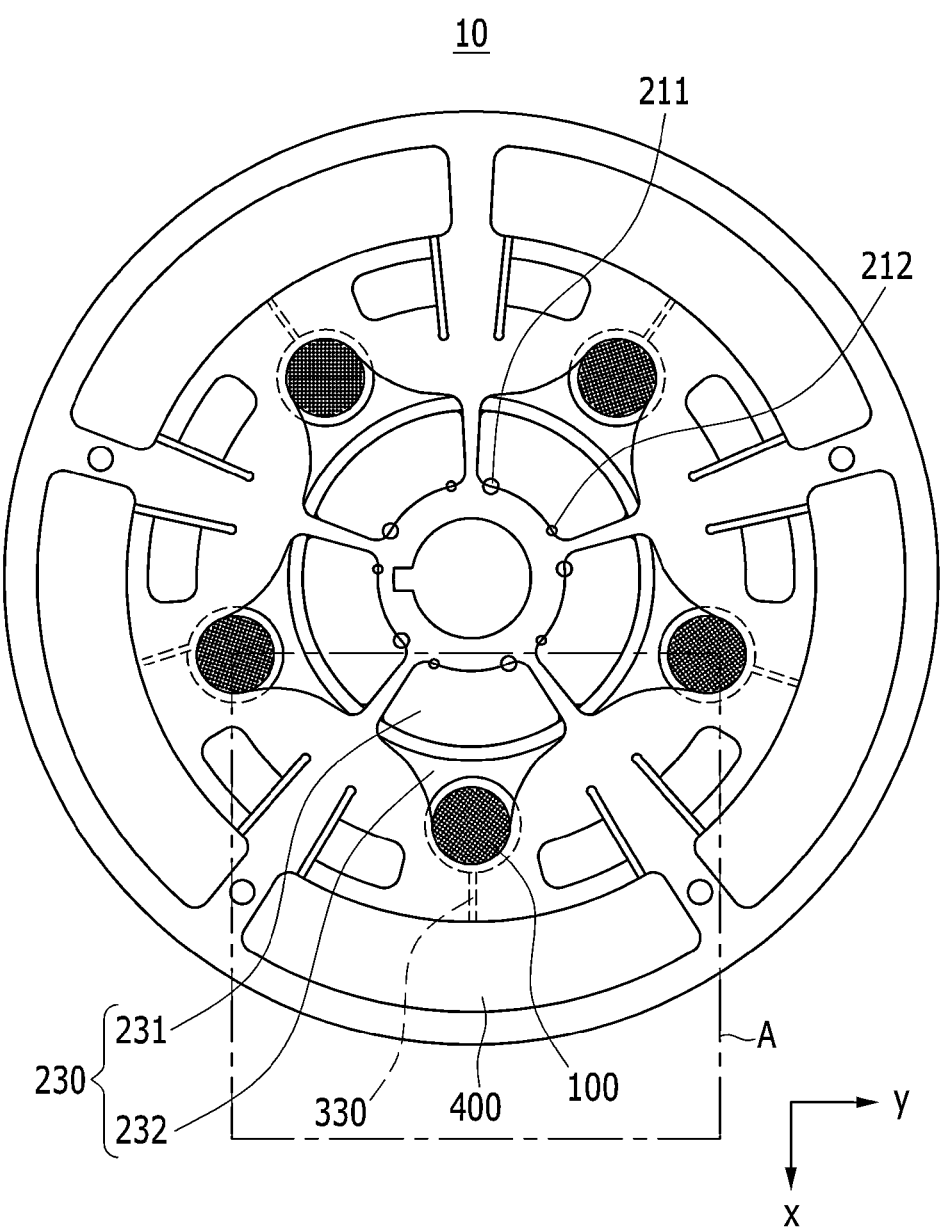
FIG. 2 is a drawing illustrating the rare cell isolation device according to the first exemplary embodiment of the present invention.
Figure 3:
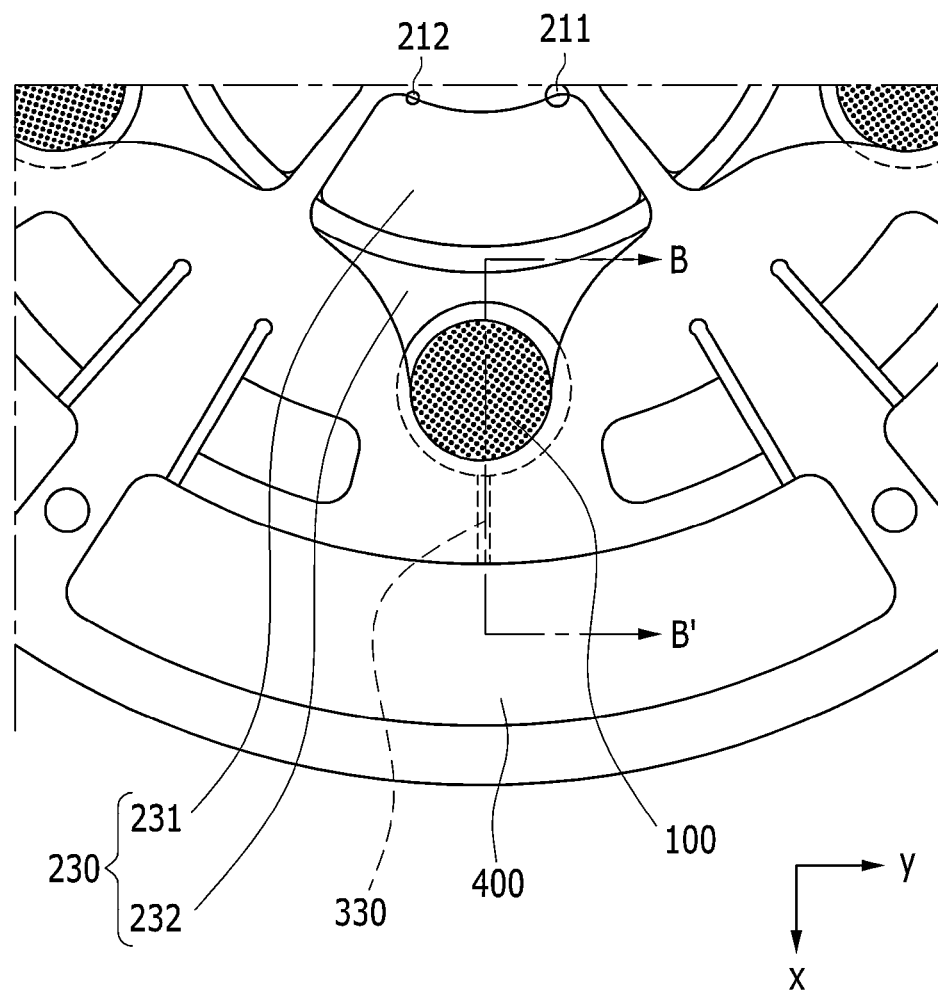
FIG. 3 is an enlarged view of a portion A of FIG. 2.
Figure 4:
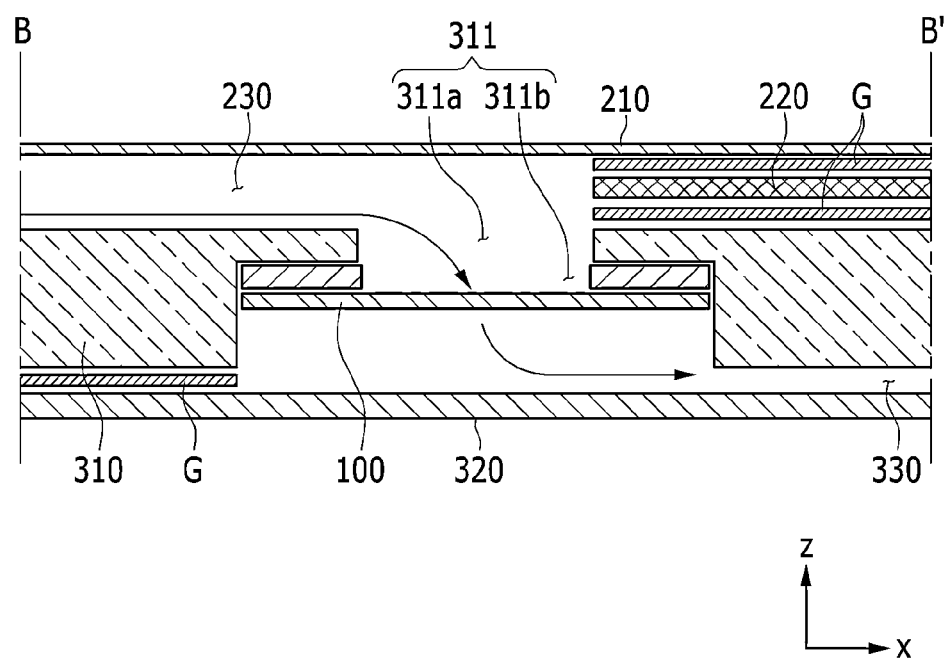
FIG. 4 is a cross-sectional view of a portion B-B' of FIG. 3.

FIG. 2 is a drawing illustrating the rare cell isolation device according to the first exemplary embodiment of the present invention, FIG. 3 is an enlarged view of a portion A of FIG. 2, and FIG. 4 is a cross-sectional view of a portion B-B' of FIG. 3.

Referring to FIG. 2 to FIG. 4, the rare cell isolation device 10 in which the upper plate 210, the first intermediate plate 220, the second intermediate plate 310, and the lower plate 320 are sequentially stacked is illustrated. Herein, in the upper plate 210 of the rare cell isolation device 10 according to the first exemplary embodiment of the present invention, the first inlet 211 and a ventilation hole 212 may be formed.

As illustrated in FIG. 2 and FIG. 3, the first inlet 211 may be formed to penetrate through the upper plate 210. In the rare cell isolation device 10 according to the first exemplary embodiment of the present invention, a biospecimen for rare cell isolation may be injected into the first body 200 through the first inlet 211. Further, as illustrated in FIG. 2, there may be multiple first inlets 211 formed in a radial direction based on the center of the first body 200. Thus, a biospecimen can be injected into the first body 200 from various directions.

Meanwhile, as illustrated in FIG. 2, the first inlet 211 may be disposed between the center of the first body 200 and the filtration membrane 100. Thus, if the first body 200 and the second body 300 are rotated, the biospecimen injected through the first inlet 211 can be easily moved to the filtration membrane 100 by centrifugal force.

As illustrated in FIG. 2 and FIG. 3, the ventilation hole 212 may be formed to penetrate through the upper plate 210. As illustrated in FIG. 2, the ventilation hole 212 may be formed so as to be adjacent to the first inlet 211 on the first body 200. Thus, when a biospecimen is injected through the first inlet 211, air present within the body 200 can be easily discharged to the outside of the first body 200.

Referring to FIG. 2 to FIG. 4 again, a first guiding unit 230 connected to the first inlet 211 may be formed between the upper plate 210 and the first intermediate plate 220 of the rare cell isolation device 10 according to the first exemplary embodiment of the present invention. As illustrated in FIG. 4, the first guiding unit 230 may guide the biospecimen injected into the first body 200 through the first inlet 211 to the filtration membrane 100.

Meanwhile, the first guiding unit 230 may be formed to penetrate through the first intermediate plate 220. That is, as illustrated in FIG. 4, the first guiding unit 230 may be formed between the upper plate 210 and the second intermediate plate 320. Thus, the biospecimen flowing through the first inlet 211 may be accommodated in the first guiding unit 230.

Further, as illustrated in FIG. 2, the first guiding unit 230 may be formed in an opposite direction to the center of the first body 200 based on the first inlet 211. Furthermore, as illustrated in FIG. 2, there may be multiple first guiding units 230 formed in a radial direction of the first body 200. Thus, when the rare cell isolation device 10 is rotated, the biospecimen may be guided more rapidly by centrifugal force in a radial direction of the first body 200.

Meanwhile, the first guiding unit 230 includes a first portion 231 and a second portion 232.

The first portion 231 is formed to penetrate through the first intermediate plate 220. Herein, as illustrated in FIG. 2 and FIG. 3, the first portion 231 may be formed to be gradually decreased in width in a radial direction of the first body 200 based on the center of the first body 200. Thus, fluid resistance of the biospecimen flowing into the first portion 231 through the first inlet 211 can be minimized.

Meanwhile, the first portion 231 according to the first exemplary embodiment of the present invention has a cross-section formed with a circular arc shape based on the center of the first body 200 as illustrated in FIG. 2, but the present invention is not necessarily limited to such a shape.

The second portion 231 is formed to penetrate through the first intermediate plate 220, and may be formed to be gradually decreased in width toward the outside in a radial direction of the first body 200 from an end of the first portion 231 based on the center of the first body 200. Thus, it is easy to collect the biospecimen guided to the second portion 232 via the first portion 231 at an end portion of the second portion 232 based on the center of the first body 200.

Referring to FIG. 2 to FIG. 4 again, a penetrating portion 311 may be formed in the second intermediate plate 310 of the rare cell isolation device 10 according to the first exemplary embodiment of the present invention.

The penetrating portion 311 may be formed at the second intermediate plate 310 in contact with the first guiding unit 230. Herein, as illustrated in FIG. 4, the penetrating portion 311 may be formed to penetrate through the second intermediate plate 310 in contact with the second portion 232. Thus, the biospecimen guided to the second portion 232 may pass through the penetrating portion 311 in an arrow direction of FIG. 4 and move toward the lower plate 320.

Meanwhile, the penetrating portion 311 of the rare cell isolation device 10 according to the first exemplary embodiment of the present invention may include a first hole 311a and a second hole 311b.

The first hole 311a may be formed at an upper part of the second intermediate plate 310 in contact with the second portion 311b. Herein, the first hole 311a may have a cross-section formed in a circular shape as illustrated in FIG. 2 and FIG. 3.

The second hole 311b is formed at a lower part of the second intermediate plate 310, and may be formed in a concentric circular shape having a cross-section with a greater exterior diameter than the first hole 311a as illustrated in FIG. 2 and FIG. 3.

Herein, the filtration membrane 100 of the rare cell isolation device 10 according to the first exemplary embodiment of the present invention may be formed to have a cross-section corresponding to the second hole 311b so that the filtration membrane 100 can be downwardly inserted into the second hole 311b as illustrated in FIG. 1 to FIG. 4. Thus, the biospecimen guided to the second portion 232 can be filtered.

As such, the rare cell isolation device 10 according to the first exemplary embodiment of the present invention can maximize an amount of the biospecimen flowing into the filtration membrane 100 since the filtration membrane 100 is downwardly inserted into the second hole 311b and bonded to a lower side of the second intermediate plate 320. Further, as illustrated in FIG. 4, since a stepped portion is formed between the filtration membrane 100 and the second portion 232, it is possible to prevent backflow of rare cells remaining in an upper part of the filtration membrane 100 to the first guiding unit 230 due to rotation of the rare cell isolation device 10 during filtering.

Meanwhile, there may be multiple filtration membranes 100 bonded to a lower side of the second intermediate plate 320 in a radial direction of the second body 300 as illustrated in FIG. 2 and FIG. 3. Thus, the biospecimen flowing into the first body 200 can be dispersed and rare cells can be isolated from each filtration membrane 100, such that filtering efficiency can be improved.

Referring to FIG. 1 to FIG. 4, the rare cell isolation device 10 according to the first exemplary embodiment of the present invention may be formed between the first body 200 and the second body 300, and may include a filtrate storage unit 400 where a filtrate filtered through the filtration membrane 100 is stored. Herein, referring to FIG. 1 and FIG. 2, the filtrate storage unit 400 may be a space formed within the rare cell isolation device 10 between the upper plate 210 and the lower plate 320 due to coupling of the first body 200 and the second body 300, but the present invention is not necessarily limited to such a configuration.

Meanwhile, the filtrate storage unit 400 may be formed in an opposite direction to the center of the first body 200 based on the filtration membrane 100. That is, the filtrate storage unit 400 is formed in a B' direction of FIG. 4 so that the filtrate storage unit 400 can accommodate a filtrate passing through the filtration membrane 100 in an arrow direction of FIG. 4. As illustrated in FIG. 2, there may be multiple filtrate storage units 400 formed into a circular arc shape within the rare cell isolation device 10.

Herein, as illustrated in FIG. 4, a first flow path 330 may be formed between the second intermediate plate 310 and the lower plate 320, and may supply the filtrate passing through the filtration membrane 100 to the filtrate storage unit 400. Herein, the first flow path 330 of the rare cell isolation device 10 according to the first exemplary embodiment of the present invention may have a width of 1 mm or less and a height of 1 mm or less so that a filtrate can pass through the first flow path 330 and backflow of the filtrate toward the filtration membrane 100 can be prevented, but the present invention is not necessarily limited thereto.

Meanwhile, the first flow path 330 of the rare cell isolation device 10 according to the first exemplary embodiment of the present invention may be formed on a side of an adhesive layer which bonds the second intermediate plate 310 and the lower plate 320 to each other among the adhesive layers G of FIG. 4, but the present invention is not necessarily limited thereto, and the first flow path 330 may be formed at a lower side of the second intermediate plate 310 or an upper side of the lower plate 320.

Hereinbefore, the configuration of the rare cell isolation device 10 according to the first exemplary embodiment of the present invention has been explained. Hereinafter, a rare cell isolation method using the rare cell isolation device 10 according to the first exemplary embodiment of the present invention will be explained.

Figure 5:
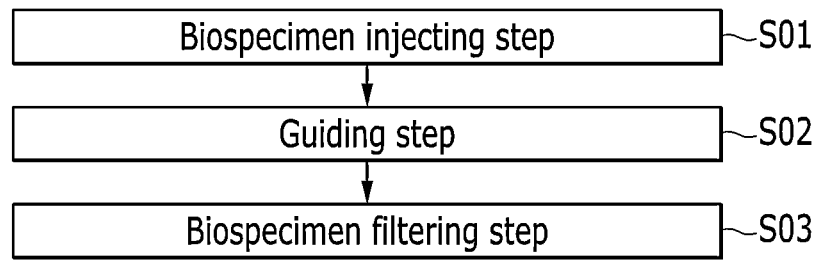
FIG. 5 is a flowchart illustrating a rare cell isolation method using the rare cell isolation device according to the first exemplary embodiment of the present invention.

FIG. 5 is a flowchart illustrating a rare cell isolation method using the rare cell isolation device according to the first exemplary embodiment of the present invention.

Referring to FIG. 5, the rare cell isolation method using the rare cell isolation device 10 according to the first exemplary embodiment of the present invention may include: a step S01 of injecting a biospecimen into the rare cell isolation device 10; a step S02 of guiding the biospecimen to the filtration membrane 100 by generating centrifugal force; and a step S03 of filtering the biospecimen through the filtration membrane 100.

Figure 6:
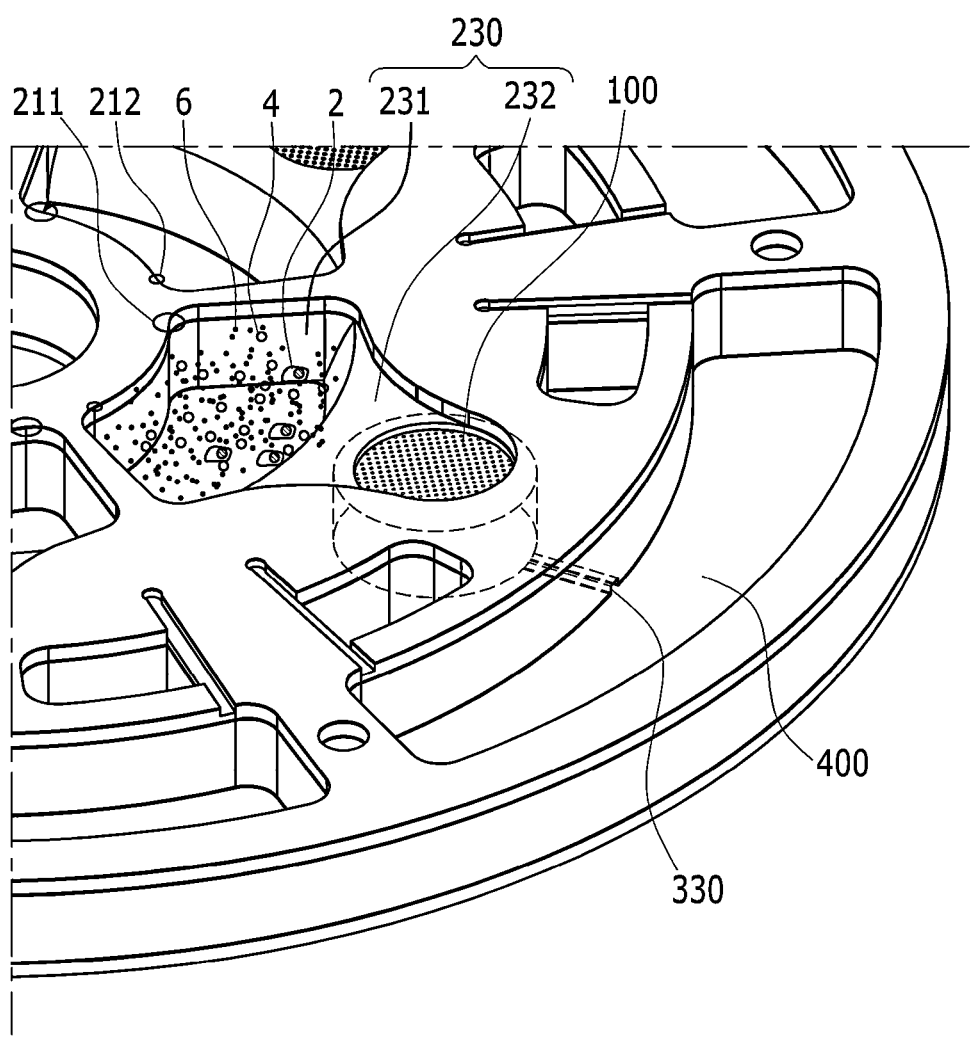
FIG. 6 is a drawing illustrating a status where a biospecimen of the rare cell isolation device according to the first exemplary embodiment of the present invention is injected into a first body.
Figure 7:
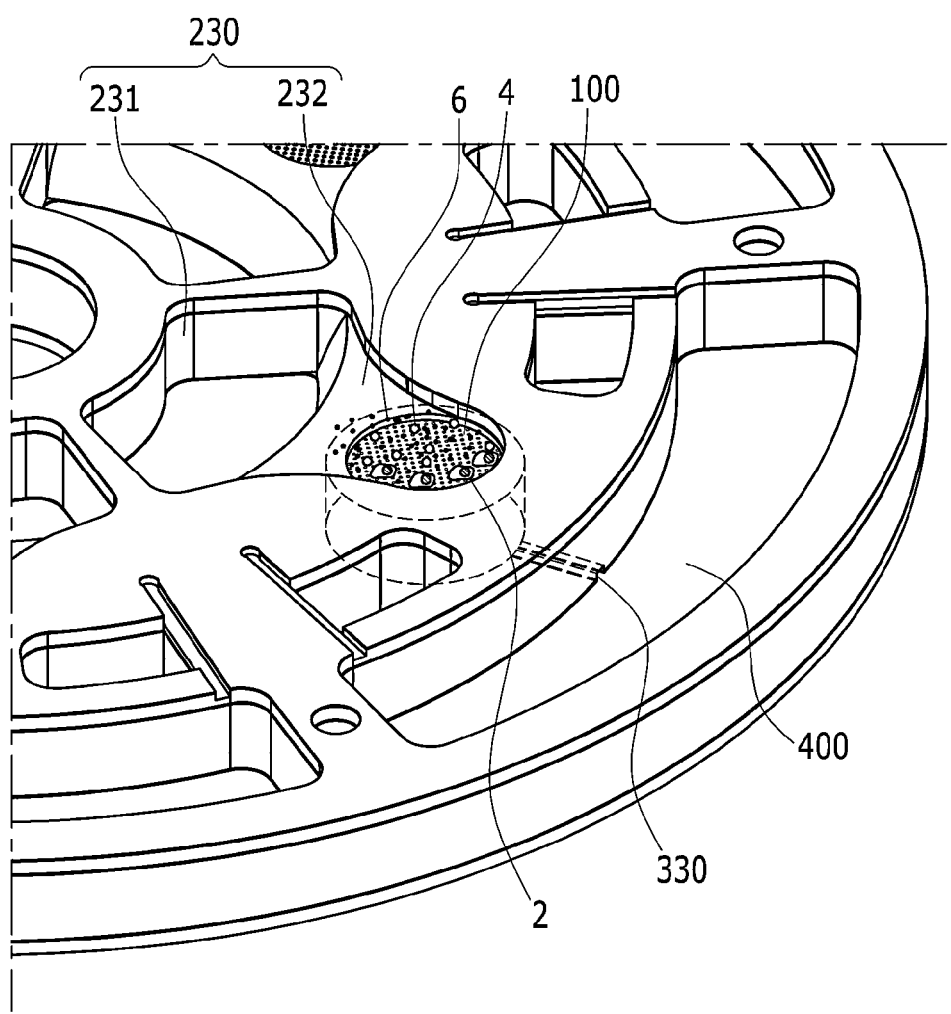
FIG. 7 is a drawing illustrating a status where a biospecimen of the rare cell isolation device according to the first exemplary embodiment of the present invention reaches a filtration membrane.

FIG. 6 is a drawing illustrating a status where a biospecimen of the rare cell isolation device according to the first exemplary embodiment of the present invention is injected into a body, and FIG. 7 is a drawing illustrating a status where a biospecimen of the rare cell isolation device according to the first exemplary embodiment of the present invention reaches a filtration membrane.

Figure 8:
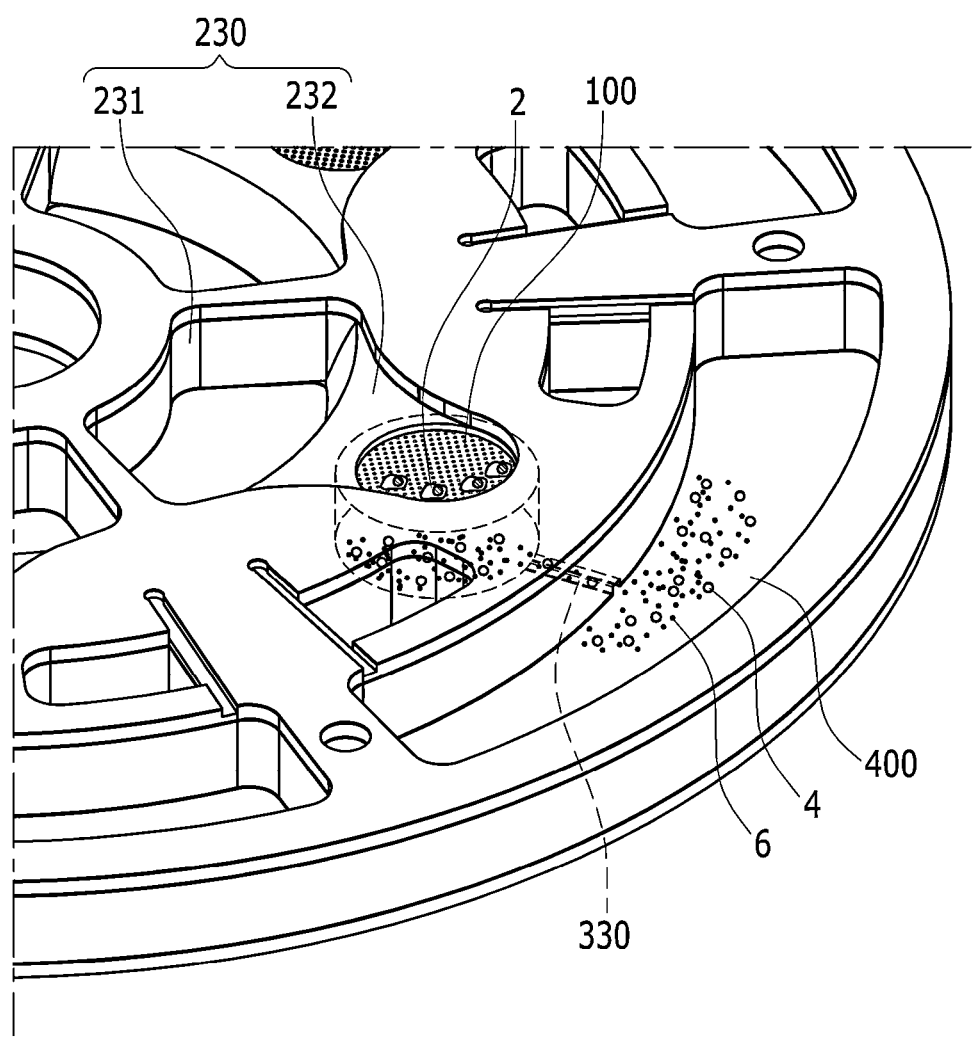
FIG. 8 is a drawing illustrating a status where the biospecimen of the rare cell isolation device according to the first exemplary embodiment of the present invention is filtered through the filtration membrane.
Figure 9:
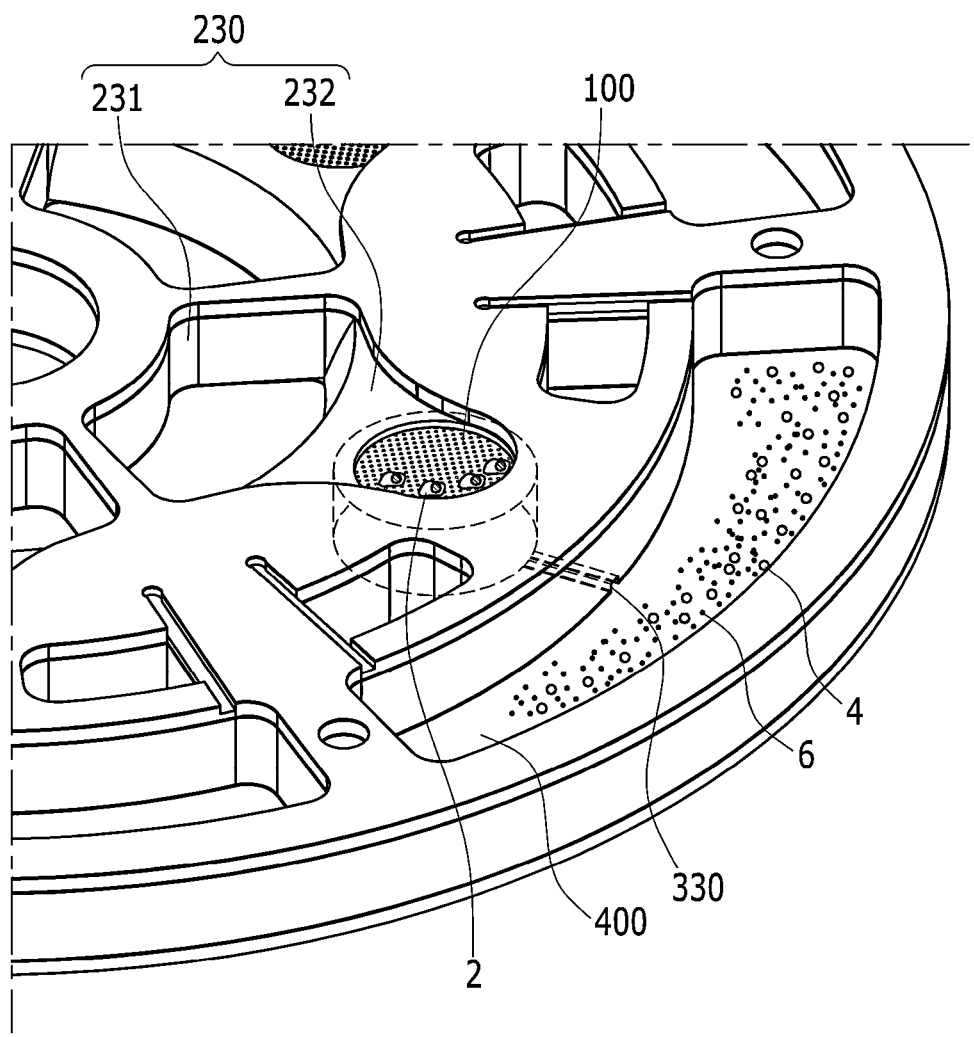
FIG. 9 is a drawing illustrating a status where filtering of the biospecimen of the rare cell isolation device according to the first exemplary embodiment of the present invention is completed.

FIG. 8 is a drawing illustrating a status where the biospecimen of the rare cell isolation device according to the first exemplary embodiment of the present invention is filtered through the filtration membrane, and FIG. 9 is a drawing illustrating a status where filtering of the biospecimen of the rare cell isolation device according to the first exemplary embodiment of the present invention is completed.

Referring to FIG. 5 to FIG. 9, in the biospecimen injecting step S01, the biospecimen is injected into the rare cell isolation device 10 through the first inlet 211. Herein, in the first exemplary embodiment of the present invention, a whole blood specimen containing circulating tumor cells is used as the biospecimen, and thus the injected biospecimen is present in the first guiding unit 230 as a mixture of circulating tumor cells 2, white blood cells 4, and red blood cells 6 as illustrated in FIG. 6.

In the guiding step S02, the rare cells present in the first guiding unit 230 are guided to the filtration membrane 100. In the first exemplary embodiment of the present invention, centrifugal force may be generated by rotating the rare cell isolation device 10 in order to rapidly guide the biospecimen. The biospecimen guided by the above-described method is disposed at an upper part of the filtration membrane 100 as illustrated in FIG. 7.

In the filtering step S03, the biospecimen guided to the upper part of the filtration membrane 100 is filtered. Herein, the circulating tumor cells 2 having relatively large molecular sizes remain in the upper part of the filtration membrane 100, and the white blood cells 4 and red blood cells 6 having relatively small molecular sizes pass through the filtration membrane 100 and move to the filtrate storage unit 400 along the first flow path 330 as illustrated in FIG. 8.

The rare cell isolation device 10 may accelerate filtering of the biospecimen by continuous rotation in the filtering step S03. In the first exemplary embodiment of the present invention, if a rotation speed of the rare cell isolation device 10 is less than 1200 rpm, it is difficult for a filtrate to move to the filtrate storage unit 400 due to fluid resistance applied to the first flow path 330. If a rotation speed of the rare cell isolation device 10 is more than 3600 rpm, leakage of the whole blood specimen may occur or the circulating tumor cells 2 may be damaged. Thus, a rotation speed of the rare cell isolation device 10 is preferably 1200 rpm to 3600 rpm or less. However, a rotation speed of the rare cell isolation device 10 of the present invention is not necessarily limited to the range as illustrated above, and may vary depending on a kind or an amount of a biospecimen to be injected.

After the filtering step S03 is completed, the circulating tumor cells 2 remain in the upper part of the filtration membrane 100 as illustrated in FIG. 9, and all of the white blood cells 4 and red blood cells 6 can be stored in the filtrate storage unit 400.

Figure 10:
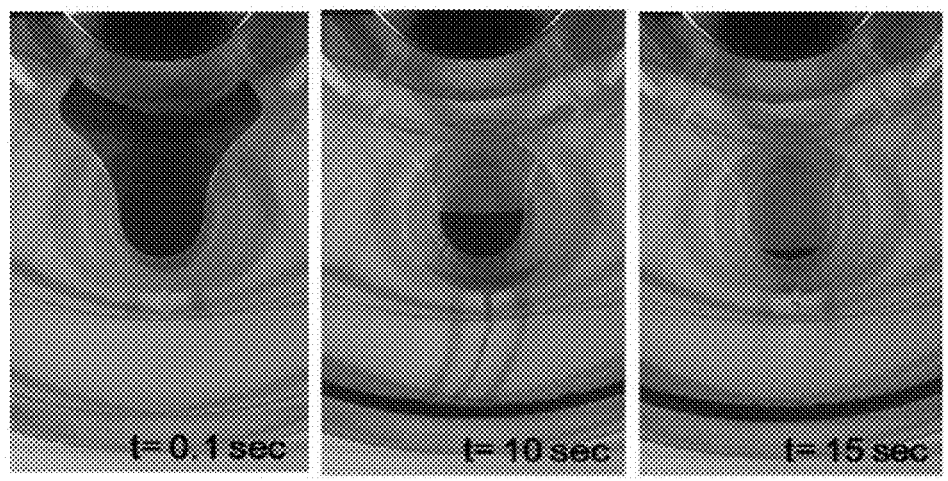
FIG. 10 is a photo illustrating a process of filtering a biospecimen using the rare cell isolation device according to the first exemplary embodiment of the present invention.

FIG. 10 shows photos illustrating a process of filtering a biospecimen using the rare cell isolation device according to the first exemplary embodiment of the present invention.

In the first exemplary embodiment of the present invention, 1 mL of the whole blood specimen containing the circulating tumor cells is injected into the body as illustrated in FIG. 10. The whole blood specimen is filtered through the filtration membrane. Herein, the circulating tumor cells remain in the upper part of the filtration membrane, and the remaining whole blood specimen including the white blood cells and the red blood cells is discharged through a lower side of the filtration membrane and moves to the filtrate storage unit along the first flow path. Herein, the rare cell isolation device is rotated around the center, thereby accelerating the guiding and filtering processes of the whole blood specimen. As a result thereof, it takes about 15 seconds to isolate all of the circulating tumor cells from the whole blood specimen.

As such, the rare cell isolation method using the rare cell isolation device 10 according to the first exemplary embodiment of the present invention has an effect of reducing a time for guiding and filtering of a biospecimen using centrifugal force, unlike the conventional microchip-based cell isolation device.

Hereinafter, a rare cell isolation device 10' according to a second exemplary embodiment of the present invention will be explained. Regarding the rare cell isolation device 10' according to the second exemplary embodiment of the present invention, a detailed description of the same components as those of the rare cell isolation device 10 according to the first exemplary embodiment of the present invention will be omitted.

Figure 11:
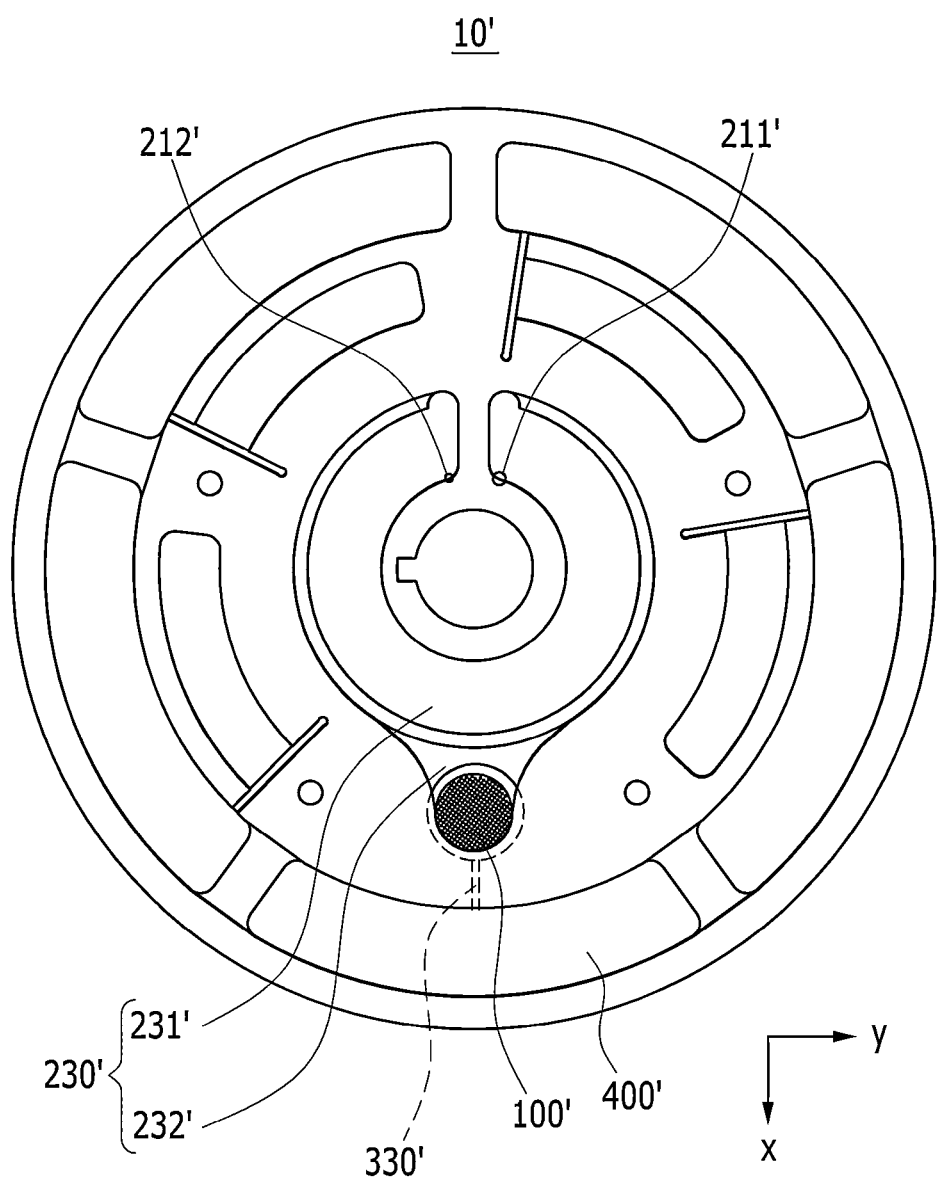
FIG. 11 is a drawing illustrating a rare cell isolation device according to a second exemplary embodiment of the present invention.

FIG. 11 is a drawing a illustrating a rare cell isolation device according to a second exemplary embodiment of the present invention.

Referring to FIG. 11, the rare cell isolation device 10' according to the second exemplary embodiment of the present invention may be formed into a circular arc shape in which a first portion 231' surrounds a center of a first body 200'. As such, the rare cell isolation device 10' according to the second exemplary embodiment of the present invention increases an amount of a biospecimen accommodated therein through the first portion 231', and thus it has an effect of increasing capture efficiency of rare circulating tumor cells with a ratio of one circulating tumor cell to one hundred million blood cells.

Hereinafter, a rare cell isolation device 10" according to a third exemplary embodiment of the present invention will be explained. Regarding the rare cell isolation device 10" according to the third exemplary embodiment of the present invention, a detailed description of the same components as those of the rare cell isolation device 10 according to the first exemplary embodiment of the present invention will be omitted.

Figure 12:
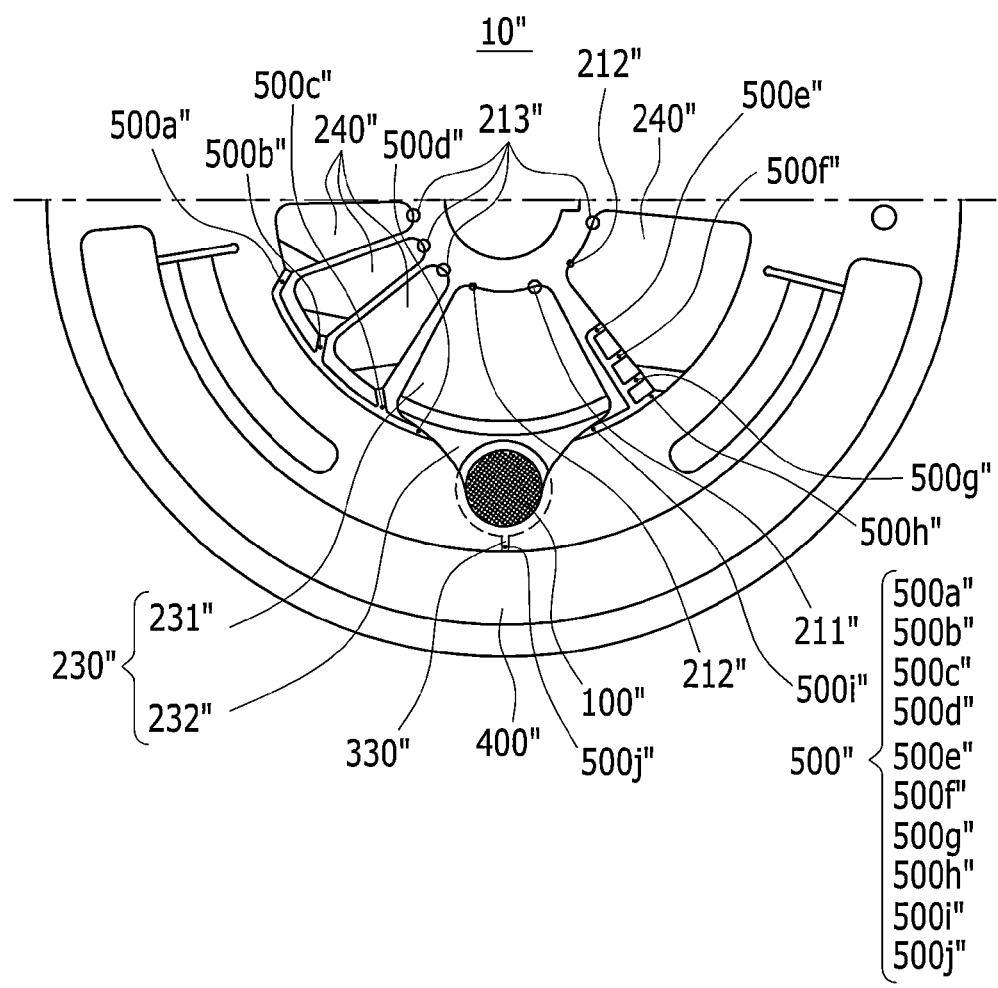
FIG. 12 is a drawing illustrating a rare cell isolation device according to a third exemplary embodiment of the present invention.

FIG. 12 is a drawing a illustrating a rare cell isolation device according to a third exemplary embodiment of the present invention.

Referring to FIG. 12, the rare cell isolation device 10" according to the third exemplary embodiment of the present invention further includes a second inlet 213" which penetrates through the upper plate and a second guiding unit 240" which is formed at the first intermediate plate.

As illustrated in FIG. 12, the second inlet 213" may be disposed on a central side of a first body 200". Herein, there may be multiple second inlets 213" formed in a radial direction based on a center of the first body 200". Further, when a fluid is injected through the second inlets 213", a ventilation hole 212" may be disposed around the second inlets 213" so that air within the body can be discharged.

As illustrated in FIG. 12, one side of a second guiding unit 240" may be connected to the second inlets 213" and the other side thereof may be connected to a second portion 232". Herein, there may be multiple second guiding units 240" so as to correspond to the plurality of the second inlets 213" and formed in the radial direction based on the center of the first body 200". Further, as illustrated in FIG. 12, there may be multiple second inlets 213" and second guiding units 240" disposed on both sides of a first guiding unit 230" based on the center of the first body 200".

In addition, the second guiding unit 240" of the rare cell isolation device 10" according to the third exemplary embodiment of the present invention has a cross-section formed in a circular arc shape corresponding to a first portion 231", but the present invention is not necessarily limited to such a shape.

Therefore, through at least one of the second inlets 213" of the rare cell isolation device 10" according to the third exemplary embodiment of the present invention, a washing solution may be injected to wash rare cells remaining in a filtration membrane 100", and through at least one of the second inlets 213", a staining reagent for staining the rare cells may be injected. The washing solution of the rare cell isolation device 10" according to the third exemplary embodiment of the present invention is a publicly-known buffer solution capable of washing rare cells without damaging them, but the present invention is not necessarily limited thereto.

Herein, the staining reagent in the present invention includes a pre-treatment reagent used for a staining step for detecting rare cells, and may include a fixation solution for fixing rare cells, permeabilization solution for Permeabilizing the rare cells, and a staining solution for staining the rare cells.

In the rare cell isolation device 10" according to the third exemplary embodiment of the present invention the present invention, referring to FIG. 12, the fixation solution, the permeabilization solution, and the staining solution are respectively injected through three second inlets formed on the left side of a first inlet 211", and the washing solution is injected through the second inlet 213" formed on the right side of the first inlet 211", but the present invention is not necessarily limited thereto.

As such, the rare cell isolation device 10" according to the third exemplary embodiment of the present invention can wash and stain rare cells remaining in the filtration membrane 100" after the filtering step, and thus it is possible to directly detect the rare cells using an optical detector without disassembling the device.

Meanwhile, a first flow path 330", a second flow path 340", or at least one of a plurality of third flow paths connecting the first guiding unit 230" and the second guiding unit 240" of the rare cell isolation device 10" according to the third exemplary embodiment of the present invention may be provided with reversible valves 500". With this configuration, a flow rate flowing into the filtration membrane 100" and a flow rate discharged from the filtration membrane 100" can be adjusted.

Herein, the reversible valves 500" may be publicly-known mechanical valves using screws or magnets, and thus a detailed description of the reversible valves will be omitted.

As illustrated in FIG. 12, the reversible valves 500" of the rare cell isolation device 10" according to the third exemplary embodiment of the present invention are provided at a microflow path connecting the second guiding unit 240" and the second portion 232", and include valves 500a" to 500d" for adjusting a flow rate of the staining reagent, valves 500e" to 500i" for adjusting a flow rate of the washing solution, and a valve 500j" provided on one side of the first flow path 330" for adjusting a flow rate of a filtrate discharged to a filtrate storage unit 400".

As such, the rare cell isolation device 10" according to the third exemplary embodiment of the present invention is provided with the reversible valves 500" within the first body 200" and the second body 300", and thus a rare cell washing and staining process can be organically controlled.

Hereinafter, a rare cell detection method using the rare cell isolation device 10" according to the third exemplary embodiment of the present invention will be explained.

Figure 13:
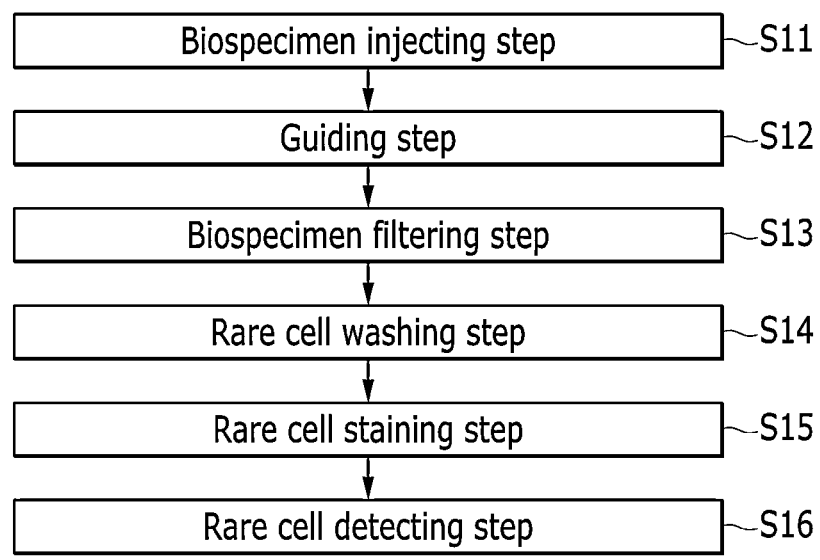
FIG. 13 is a flowchart illustrating a rare cell detection method using the rare cell isolation device according to the third exemplary embodiment of the present invention.

FIG. 13 is a flowchart illustrating a rare cell detection method using the rare cell isolation device according to the third exemplary embodiment of the present invention.

Referring to FIG. 12 and FIG. 13, the rare cell detection method using the rare cell isolation device 10" according to the third exemplary embodiment of the present invention may include: a step S11 of injecting a biospecimen into the rare cell isolation device 10"; a step S12 of guiding the biospecimen to the filtration membrane 100" by rotating the rare cell isolation device 10"; a step S13 of filtering the biospecimen through the filtration membrane 100"; a step S14 of washing the rare cells remaining in the filtration membrane 100"; a step S15 of staining the rare cells; and a step S16 of detecting the stained rare cells.

In the biospecimen injecting step S11, the biospecimen is injected through the first inlet 211". Herein, the biospecimen is moved to the first portion 231" from the first inlet 211". Rotation of the rare cell isolation device 10" is then stopped and all of the reversible valves 500" are closed.

In the guiding step S12, the biospecimen present in the first portion 231" is guided to the second portion 232". Herein, the rare cell isolation device 10" is rotated at a rotation speed of 1200 rpm to 3600 rpm. Thus, it is possible to accelerate guiding of the biospecimen present in the first portion 231" to the second portion 232" by centrifugal force. All of the reversible valves 500" are then closed.

In the biospecimen filtering step S13, the biospecimen guided to the second portion 232" is divided into rare cells and a filtrate through the filtration membrane 100". In the present invention, the rare cells have relatively large particle sizes, and thus they remain in an upper part of the filtration membrane, and the biospecimen filtrate passes through the filtration membrane 100" and moves to the filtrate storage unit 400" along the first flow path 300". The rare cell isolation device 10" can rotate at a rotation speed of 1200 rpm to 3600 rpm, thereby accelerating filtering of the biospecimen.

Further, in the above-described step, while the valves 500a" to 500i" of the reversible valves 500" are closed, only the valve 500j" may be opened to supply the filtrate to the filtrate storage unit 400".

In the rare cell washing step S14, rare cells remaining in the upper part of the filtration membrane 100" after the filtering step S13 are washed with the washing solution. The washing solution is accommodated in the second guiding unit 240" through a second inlet formed in the right direction based on the first inlet 211" of FIG. 11. Herein, only the valves 500e" to 500i" of the reversible valves 500" are opened and the washing solution is supplied to the filtration membrane 100" to wash the rare cells. After washing of the rare cells is completed, the valves 500e" to 500i" are closed and the valve 500j" is simultaneously opened, and thus the washing solution used for washing can be moved to the filtrate storage unit 400".

In the rare cell staining step S15, the washed rare cells are fixed, Permeabilized, and stained using the staining solution. The fixation solution, the permeabilization solution, and the staining solution are respectively injected through three second inlets formed on the left direction based on the first inlet 211" of FIG. 11. As illustrated in FIG. 11, the fixation solution, the permeabilization solution, and the staining solution may be respectively stored in three second guiding units. In the rare cell detection method using the rare cell isolation device 10" according to the third exemplary embodiment of the present invention, the fixation solution is stored in the second guiding unit on the left based on the first inlet 211" of FIG. 11, the permeabilization solution is stored in the intermediate second guiding unit, and the staining solution is stored in the adjacent second guiding unit, but the present invention is not necessarily limited to such storage positions.

Meanwhile, only the valves 500a" and 500d" of the reversible valves 500" are opened to transfer the cell fixation solution to the filtration membrane 100". After the rare cells are fixed through an incubation time, the valves 500a" and 500d" are closed and only the valve 500j" is opened to move the fixation solution used for fixation to the filtrate storage unit 400". Then, the valve 500j" is closed and only the valves 500f" and 500i" are opened to wash the fixed rare cells, and the valves 500f" and 500i" are closed and only the valve 500j" is opened to move the washing solution to the filtrate storage unit 400".

Subsequently, only the valves 500b" and 500d" are opened to transfer the permeabilization solution to the filtration membrane 100". After an incubation time, only the valve 500j" is opened to move the fixation solution to a residue accommodation chamber. Then, only the valves 500g" and 500i" are opened, and a process of washing the rare cells is carried out by the above-described method.

Then, only the valves 500c" and 500d" are opened to supply the cell staining solution to the filtration membrane 100". Herein, the rare cells may be stained with the staining solution. After staining is completed, only the valves 500h" and 500i" are opened, and a process of washing the rare cells is carried out by the above-described method.

Meanwhile, in the rare cell detection method using the rare cell isolation device 10" according to the third exemplary embodiment of the present invention, the rare cells are stained using a publicly-known immunofluorescence method, but the present invention is not necessarily limited to such a method.

In the rare cell detecting step S16, the rare cells which are completely stained within the rare cell isolation device 10" are immediately detected without disassembling the device. Herein, the first body 200" and the second body 300" of the rare cell isolation device 10" according to the third exemplary embodiment of the present invention are formed of a material having optical transmittance, and thus the stained rare cells present within the rare cell isolation device 10" can be immediately detected using an optical microscope. In the rare cell detection method using the rare cell isolation device 10" according to the third exemplary embodiment of the present invention, a fluorescence microscope is used as the optical microscope, but the present invention is not necessarily limited thereto.

As such, the rare cell detection method using the rare cell isolation device 10" according to the third exemplary embodiment of the present invention has a merit in that it can stain and directly detect rare cells within the device without disassembling the device, unlike the conventional microchip-based rare cell isolation device.

Hereinafter, a rare cell isolation device 10''' according to a fourth exemplary embodiment of the present invention will be explained. Regarding the rare cell isolation device 10''' according to the fourth exemplary embodiment of the present invention, a detailed description of the same components as those of the rare cell isolation device 10" according to the third exemplary embodiment of the present invention will be omitted.

Figure 14:
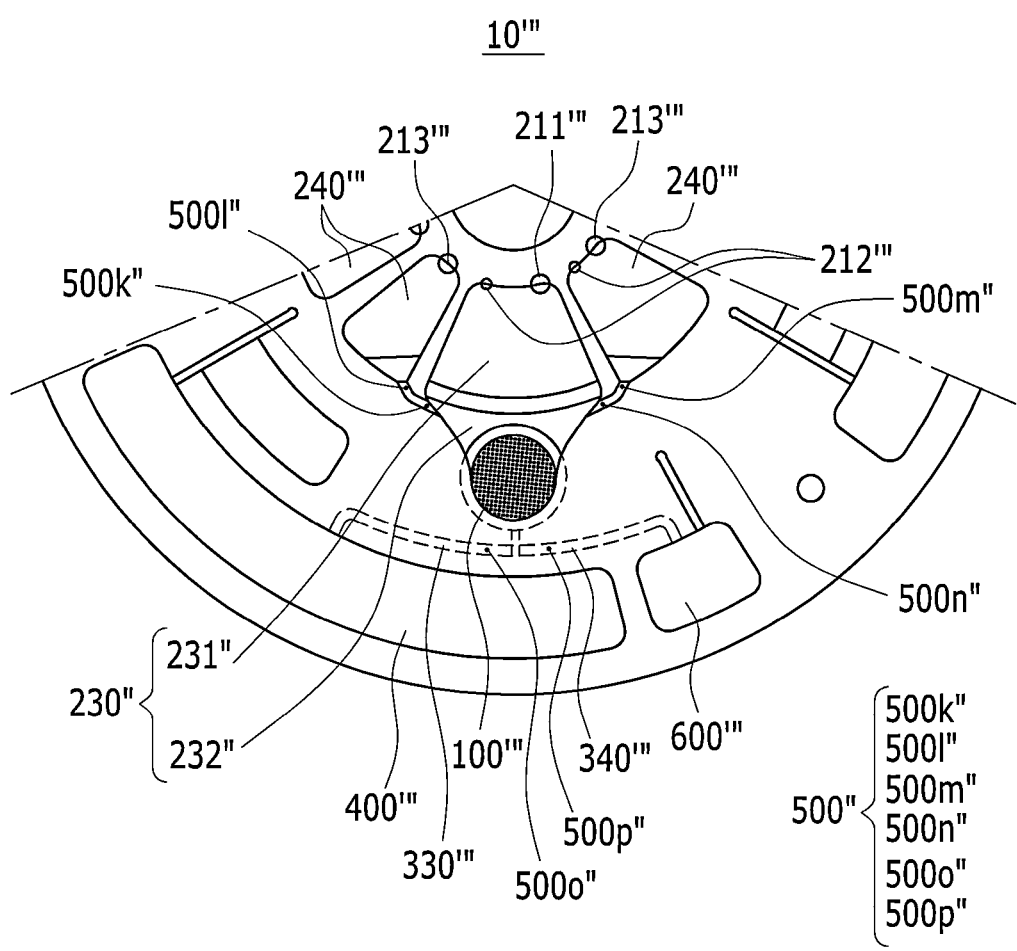
FIG. 14 is a drawing illustrating a rare cell isolation device according to a fourth exemplary embodiment of the present invention.

FIG. 14 is a drawing illustrating a rare cell isolation device according to a fourth exemplary embodiment of the present invention.

Referring to FIG. 14, in the rare cell isolation device 10''' according to the fourth exemplary embodiment of the present invention, multiple second inlets 213''' and second guiding units 240''' are formed in a radial direction based on a first body 200''', in the same manner as the rare cell isolation device 10" according to the third exemplary embodiment of the present invention.

Herein, through at least one or more of the second inlets 213''' of the rare cell isolation device 10''' according to the fourth exemplary embodiment of the present invention, a cell lysis solution may be injected instead of the staining regent of the rare cell isolation device 10" according to the third exemplary embodiment of the present invention. That is, the rare cell isolation device 10''' according to the fourth exemplary embodiment of the present invention may generate a detection solution by lysing rare cells instead of staining rare cells.

Further, in the rare cell isolation device 10''' according to the fourth exemplary embodiment of the present invention, a detection solution storage unit 600''' connected to the filtration membrane 100''' may be formed between a first body 200''' and a second body 300'''. That is, the detection solution storage unit 600''' may be a space formed within the rare cell isolation device 10''' due to coupling of the first body 200''' and the second body 300'''.

Herein, as illustrated in FIG. 12, a second flow path 340''' is branched from a first flow path 330''' and connects a filtration membrane 100''' with the detection solution storage unit 600'''. Meanwhile, the second flow path 340''' of the rare cell isolation device 10''' according to the fourth exemplary embodiment of the present invention has a width and a height so as to correspond to the first flow path 330′′′ and is formed at a third adhesive layer, but the present invention is not necessarily limited thereto.

Further, as illustrated in FIG. 14, reversible valves 500′′′ of the rare cell isolation device 10′′′ according to the fourth exemplary embodiment of the present invention are provided at a microflow path connecting the second guiding unit 240′′′ and a second portion 232′′′ and include valves 500*l*′′′ and 500*m*′′′ for adjusting a flow rate of the cell lysis solution, valves 500*n*′′′ and 500*o*′′′ for adjusting a flow rate of the washing solution, and a valve 500*p*′′′ provided on one side of the first flow path 330′′′ for adjusting a flow rate of a filtrate discharged to a filtrate storage unit 400′′′, and also a valve 500*q*′′′ provided on one side of the second flow path 340′′′ for adjusting a flow rate of the detection solution discharged to the detection solution storage unit 600′′′.

As such, the rare cell isolation device 10′′′ according to the fourth exemplary embodiment of the present invention can generate the detection solution therein by lysing the rare cells. Thus, the rare cell isolation device 10′′′ has a merit in that it can be used even when rare cell gene amplification such as a polymerase chain reaction (PCR) and a quantitative polymerase chain reaction (qPCR) is needed.

Hereinafter, a rare cell detection method using the rare cell isolation device 10′′′ according to the fourth exemplary embodiment of the present invention will be explained.

Figure 15:
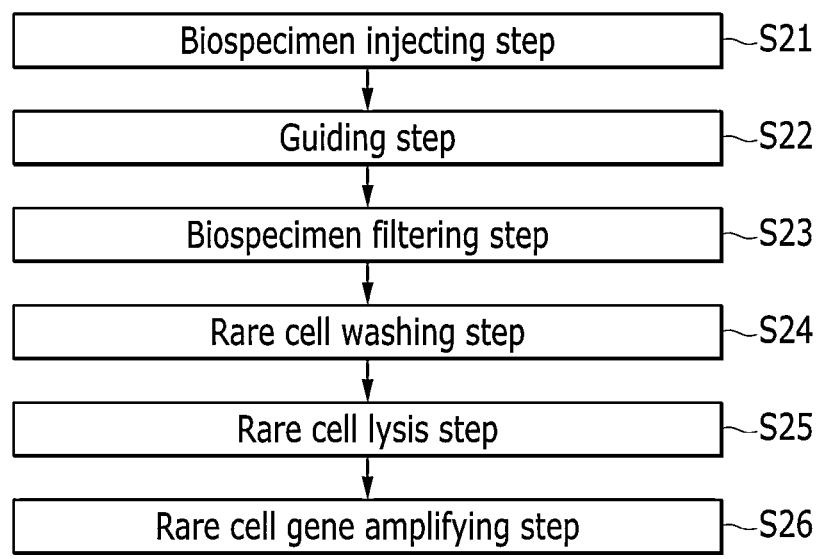
FIG. 15 is a flowchart illustrating a rare cell detection method using the rare cell isolation device according to the fourth exemplary embodiment of the present invention.

FIG. 15 is a flowchart illustrating a rare cell detection method using the rare cell isolation device according to the fourth exemplary embodiment of the present invention.

Referring to FIG. 14 and FIG. 15, the rare cell detection method using the rare cell isolation device 10′′′ according to the fourth exemplary embodiment of the present invention includes: a step S21 of injecting a biospecimen into the rare cell isolation device 10′′′; a step S22 of guiding the biospecimen into the filtration membrane 100′′′ by rotating the rare cell isolation device 10′′′; a step S23 of filtering the biospecimen through the filtration membrane 100′′′; a step S24 of washing rare cells remaining in the filtration membrane 100′′′; a step S25 of lysing the rare cells; and a step S26 of specifically amplifying genes of the lysing rare cells.

Herein, regarding the rare cell detection method using the rare cell isolation device 10′′′ according to the fourth exemplary embodiment of the present invention, the rare cell injecting step S21, the guiding step S22, and the biospecimen filtering step S23 are the same as the rare cell injecting step S11, the guiding step S12, and the biospecimen filtering step S13, respectively, of the rare cell detection method using the rare cell isolation device 10′′ according to the third exemplary embodiment of the present invention, and thus a detailed description thereof will be omitted.

In the rare cell washing step S24, rare cells remaining in an upper part of the filtration membrane 100′′′ after the filtering step S23 are washed with the washing solution. Herein, the washing solution is accommodated in the second guiding unit through a second inlet formed in the right direction based on the first inlet 211′′′ of FIG. 14. Herein, only the valves 500*m*′′′ to 500*n*′′′ of the reversible valves 500′′′ are opened and the washing solution is supplied to the filtration membrane 100′′′ to wash the rare cells. Then, after washing of the rare cells is completed, the valves 500*m*′′′ to 500*n*′′′ are closed and only the valve 500*o*′′′ is simultaneously opened, and thus the washing solution used for washing can be moved to a filtrate storage unit 400′′′.

In the rare cell lysis step S25, the cell lysis solution is supplied to the washed rare cells, and thus the rare cells can be lysed in the form of a detection solution. Herein, the cell lysis solution is accommodated in the second guiding unit through a second inlet formed in the left direction based on the first inlet 211′′′ of FIG. 13. Herein, only the valves 500*k*′′′ and 500*l*′′′ of the reversible valves 500′′′ are opened and the cell lysis solution is supplied to the filtration membrane 100′′′ to lyse the rare cells. After dissolution of the rare cells is completed through an incubation time, the valves 500*k*′′′ and 500*l*′′′ are closed and only the valve 500*p*′′′ is simultaneously opened, and thus the lysed rare cell solution can be moved to the detection solution storage unit 600′′′.

In the rare cell gene amplifying step S26, the lysed rare cell solution is used as a detection solution, and thus a gene amplifying process is carried out with the detection solution to detect the rare cells. Herein, the rare cell detection method using the rare cell isolation device 10′′′ according to the fourth exemplary embodiment of the present invention provides a polymerase chain reaction (PCR) or a quantitative polymerase chain reaction (qPCR) as a gene amplification method, but the present invention is not necessarily limited to such a method.

As such, in the rare cell detection method using the rare cell isolation device 10′′′ according to the fourth exemplary embodiment of the present invention, the isolated rare cells can be formed in the form of a detection solution, and thus the rare cell detection method has a merit in that it is possible to detect rare cells without disassembling the device even when it is necessary to detect rare cells outside the rare cell isolation device 10′′′ for diagnosis of rare cell molecules or the like.

Hereinafter, an experimental example of treating and detecting rare cells using the rare cell isolation device 10′′ according to the third exemplary embodiment of the present invention will be explained.

Figure 16:
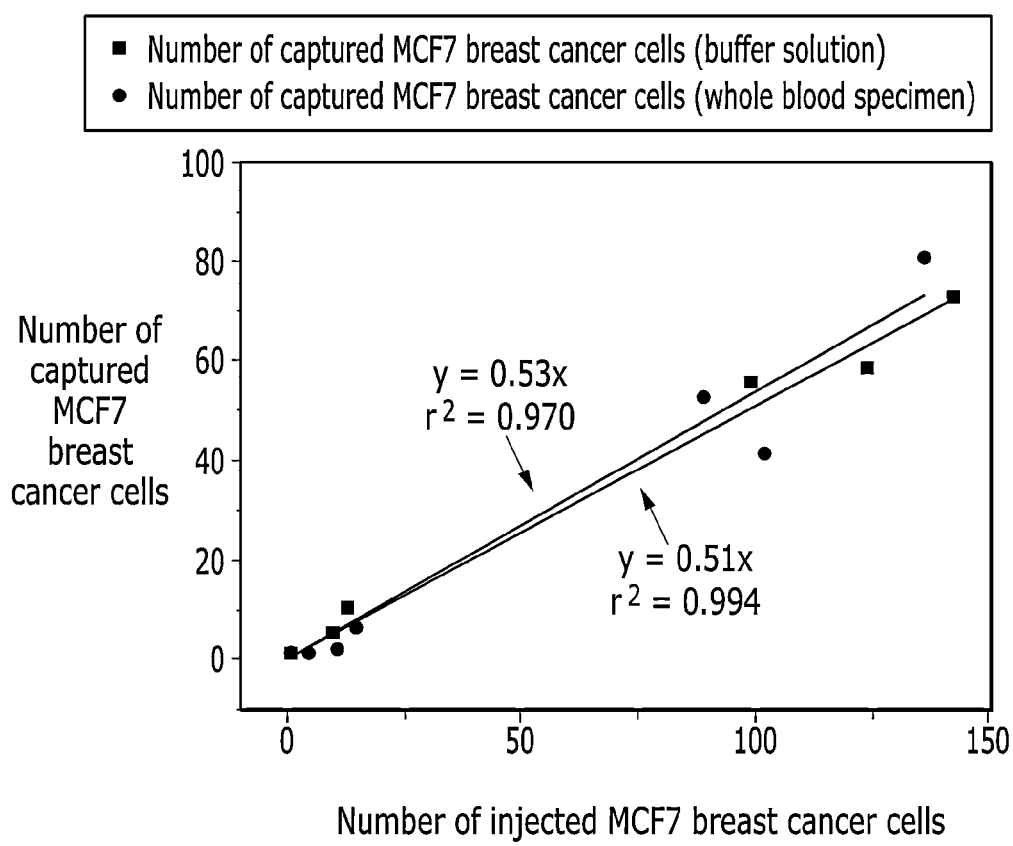
FIG. 16 is a graph illustrating capture efficiency and purity of a cancer cell depending on a rotation speed of the rare cell isolation device according to the third exemplary embodiment of the present invention.
Figure 17:
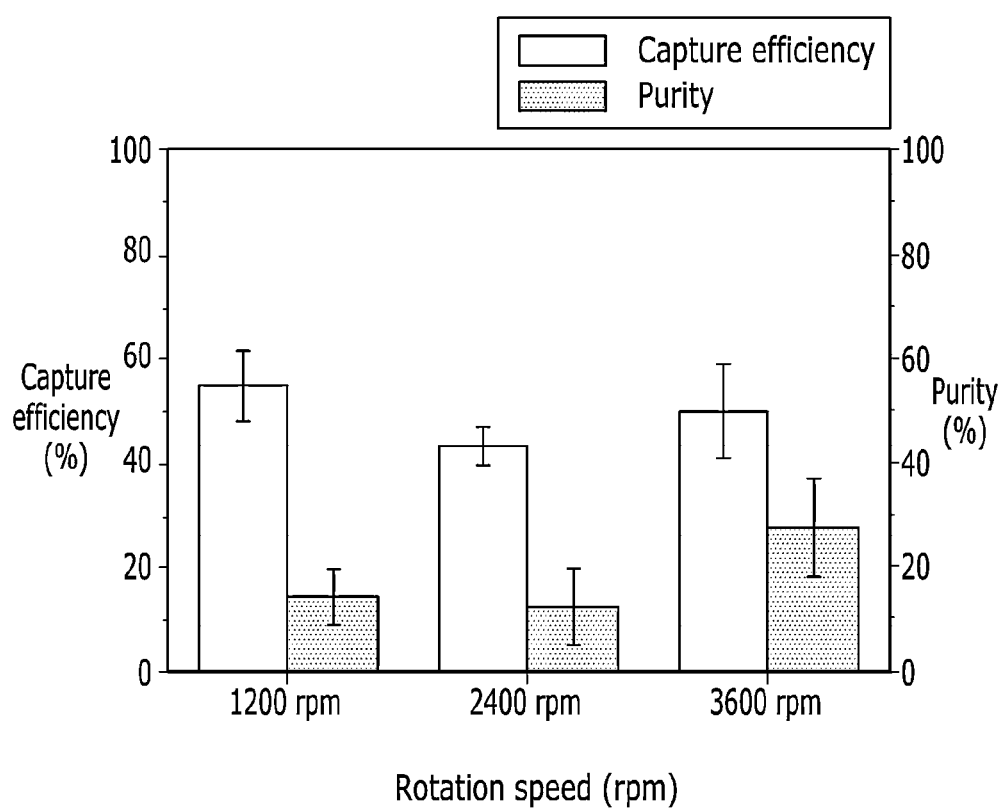
FIG. 17 is a graph illustrating a capture level depending on the number of injected MCF7 breast cancer cells of the rare cell isolation device according to the third exemplary embodiment of the present invention.
Figure 18:
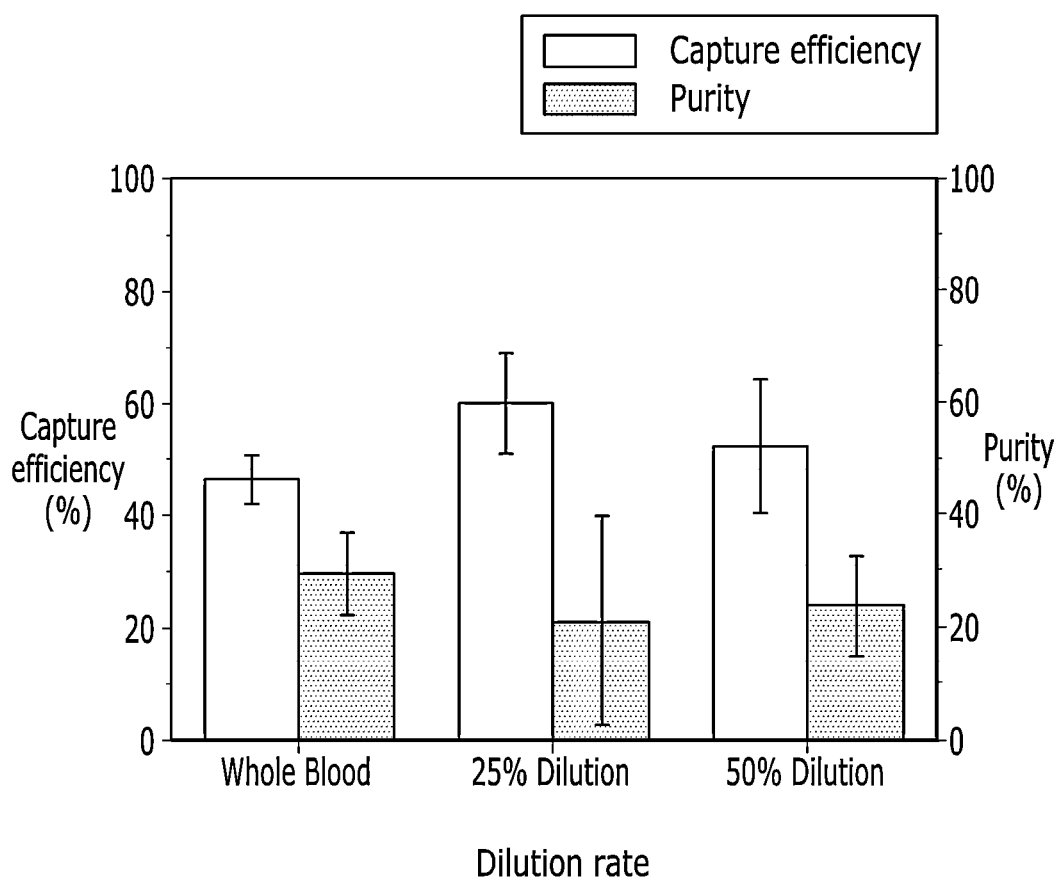
FIG. 18 is a graph illustrating capture efficiency and purity of a cancer cell depending on a dilution rate of a whole blood specimen at a rotation speed of 1200 rpm of the rare cell isolation device according to the third exemplary embodiment of the present invention.

FIG. 16 is a graph illustrating a capture level depending on a number of injected MCF7 breast cancer cells of the rare cell isolation device according to the third exemplary embodiment of the present invention, FIG. 17 is a graph illustrating capture efficiency and purity of a cancer cell depending on a rotation speed of the rare cell isolation device according to the third exemplary embodiment of the present invention, and FIG. 18 is a graph illustrating capture efficiency and purity of cancer cells depending on a dilution rate of a specimen of the rare cell isolation device according to the third exemplary embodiment of the present invention.

FIG. 16 to FIG. 18 show results of microscopic analysis of the number of isolated cancer cells after the cancer cells remaining in the filtration membrane 100′′ of the rare cell isolation device 10′′ are stained according to the third exemplary embodiment of the present invention.

<Rare Cell Isolation and Staining Process Using Rare Cell Isolation Device>

A cancer cell staining process was carried out without disassembling the rare cell isolation device 10′′. 300 μL of 4% paraformaldehyde (PFA) was used as a fixation solution, and 0.1% Triton 100-X containing a surfactant as a main component was used as a permeabilization solution to respectively fix and Permeabilize cancer cells. The cell fixation solution and the permeabilization solution were injected into the first body 200′′ through the second inlet 213′′, and a whole blood specimen was moved to the upper part of the filtration membrane 100′′ by rotating the device at 3600 rpm for 0.5 seconds. Thus, incubation can be carried out. A staining solution was also injected through the second inlet 213′′. As the staining solution, a solution including reagents such as 100 ng/mL of DAPI (for staining nuclei), 8 μg/mL of Anti-Pan-Cytokeratin-eFluor® 615 (for staining cancer cells), 240 ng/mL of Anti-Cytokeratin-PE (for staining cancer cells), and 4 μg/mL of Human CD45-FITC (for staining white blood cells) mixed at the same ratio was used.

In the present experimental example, a staining process of circulating tumor cells, a fluid state, a volume of input fluid, a rotation speed of the device, and a process time were as illustrated in Table 1.

TABLE 1

| Order | Staining process | Fluid state | Fluid volume | Rotation speed | Time | |
|---|---|---|---|---|---|---|
| 1 | Specimen filtering | Flowing | 1 mL | 2400 rpm | 15 seconds | 30 seconds |
| 2 | Washing | Flowing | 1 mL | 1200 rpm | 15 seconds | |
| 3 | Fc blocking | Stationary | 300 μL | — | 15 seconds | 50.8 minutes |
| 4 | Washing | Flowing | 500 μL | 1200 rpm | 15 seconds | |
| 5 | Fixing | Stationary | 300 μL | — | 15 seconds | |
| 6 | Permeabilizing | Stationary | 300 μL | — | 15 seconds | |
| 7 | Washing | Flowing | 500 μL | 1200 rpm | 15 seconds | |
| 8 | Staining | Stationary | 300 μL | — | 15 seconds | |
| 9 | Washing | Flowing | 500 μL | 1200 rpm | 15 seconds | |

Total process time: 51.3 minutes

<Capture Efficiency Depending on Cell Concentration of Target Cancer Cell>

FIG. 16 is a graph illustrating a capture level depending on the number of injected MCF7 breast cancer cells of the rare cell isolation device according to the third exemplary embodiment of the present invention.

Referring to FIG. 16, it can be seen that when cancer cells are injected to the washing solution (1×PBS buffer solution), capture efficiency of cancer cells was 51% according to linear regression analysis, and when cancer cells were injected to the whole blood specimen, capture efficiency of cancer cells was 53% according to linear regression analysis. Further, in both cases, according to correlation curves, determination coefficients (R-square) were 0.97 and 0.99, respectively. Thus, it can be seen that in the both cases of injecting cancer cells to the 1×PBS buffer solution and injecting cancer cells to the whole blood specimen, capture efficiencies of cancer cells using the rare cell isolation device 10" were similarly about 50%. Therefore, it can be seen that the rare cell isolation device 10" can isolate rare cells regardless of the kind of a biospecimen.

<Capture Efficiency and Purity of Cancer Cell Depending on Rotation Speed of Device>

FIG. 17 is a graph illustrating capture efficiency and purity of a cancer cell depending on a rotation speed of the rare cell isolation device according to the third exemplary embodiment of the present invention.

Referring to FIG. 17, it can be seen that when a rotation speed of the rare cell isolation device 10" was 1200 rpm, capture efficiency and purity of cancer cells were 55.2% and 14.37%, respectively, and when a rotation speed of the rare cell isolation device 10" was 2200 rpm, capture efficiency and purity of cancer cells were 43.37% and 12.39%, respectively. Further, it can be seen that when rotation speed of the rare cell isolation device 10" was 3600 rpm, capture efficiency and purity of cancer cells were 49.97% and 27.34%, respectively.

<Capture Efficiency and Purity of Cancer Cell Depending on Dilution Rate of Specimen>

FIG. 18 is a graph illustrating capture efficiency and purity of a cancer cell depending on a dilution rate of a whole blood specimen at a rotation speed of 1200 rpm of the rare cell isolation device according to the third exemplary embodiment of the present invention. Herein, the whole blood specimen was diluted with a 1×PBS (phosphate buffered saline) buffer solution.

Referring to FIG. 18, it can be seen that when a non-diluted whole blood specimen was injected, capture efficiency and purity of cancer cells were 46.68% and 29.76%, respectively, and when the whole blood specimen was diluted by 25%, capture efficiency and purity of cancer cells were 60.31% and 21.01%, respectively. Further, it can be seen that when the whole blood specimen was diluted by 50%, capture efficiency and purity of cancer cells were 52.36% and 23.68%, respectively.

<Clinical Test Result>

Figure 19:
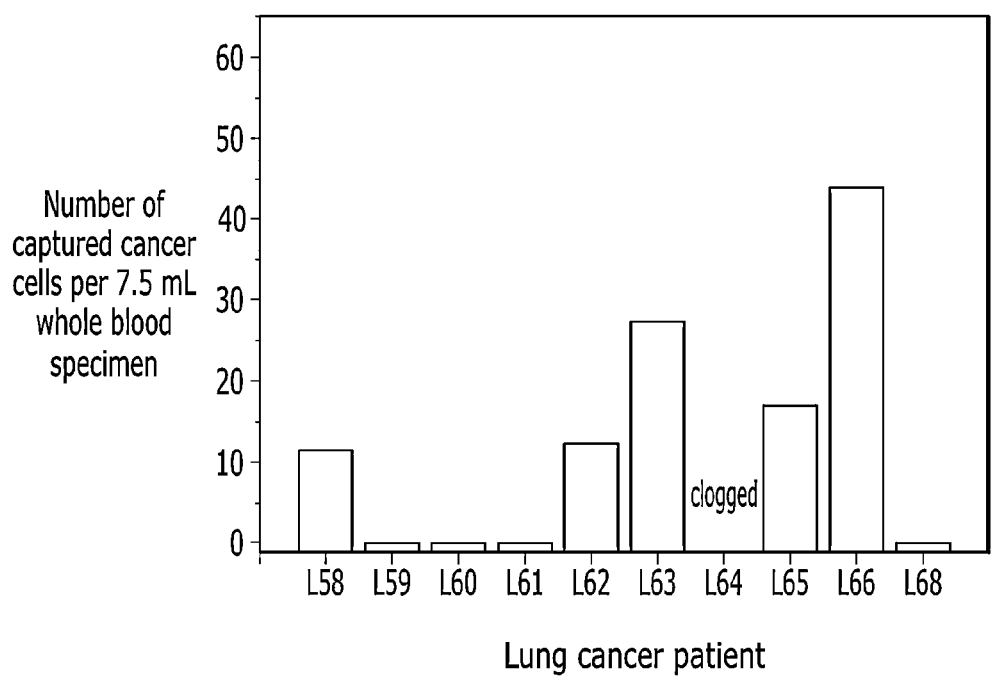
FIG. 19 is a graph illustrating the number of cancer cells per 7.5 mL of a whole blood specimen converted from the number of cancer cells detected when a whole blood specimen of a lung cancer patient group is introduced into the rare cell isolation device according to the third exemplary embodiment of the present invention.
Figure 20:
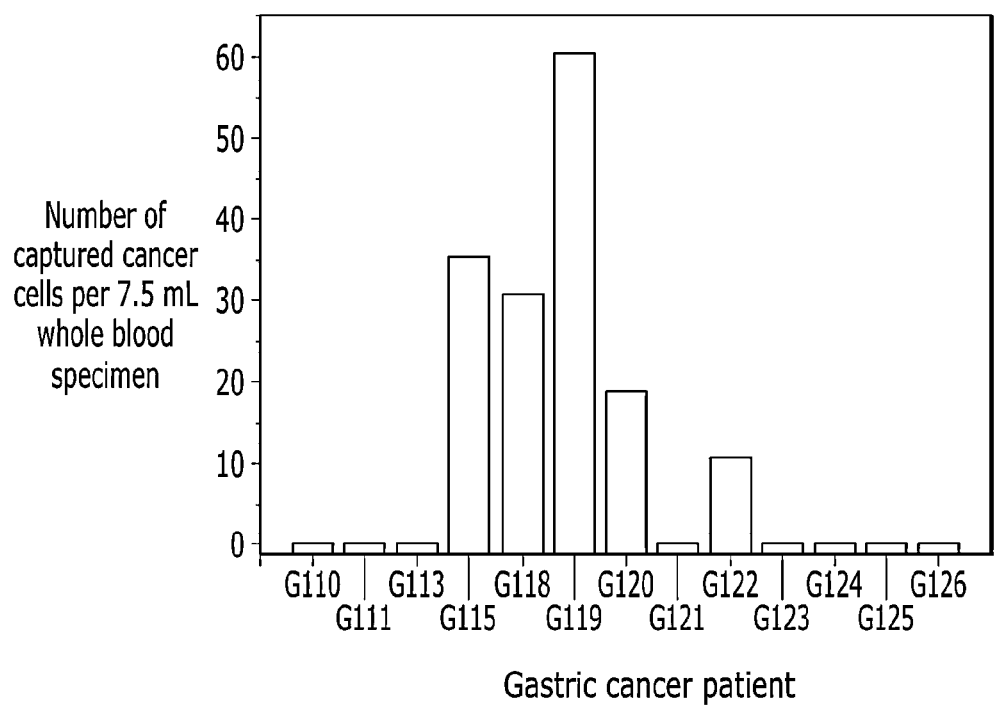
FIG. 20 is a graph illustrating the number of cancer cells per 7.5 mL of a whole blood specimen converted from the number of cancer cells detected when a whole blood specimen of a gastric cancer patient group is introduced into the rare cell isolation device according to the third exemplary embodiment of the present invention.

FIG. 19 is a graph illustrating the number of cancer cells per 7.5 mL of a whole blood specimen converted from the number of cancer cells detected when a whole blood specimen of a breast cancer patient group is introduced into the rare cell isolation device according to the third exemplary embodiment of the present invention, and FIG. 20 is a graph illustrating the number of cancer cells per 7.5 mL of a whole blood specimen converted from the number of cancer cells detected when a whole blood specimen of a gastric cancer patient group is introduced into the rare cell isolation device according to the third exemplary embodiment of the present invention.

Since a volume of blood used in a Cellsearch® system was 7.5 mL, in the present experimental example, the converted number of captured cancer cells per 7.5 mL was analyzed for comparison with the system. Herein, referring to FIG. 19 and FIG. 20, it can be seen that as for the lung cancer patient group, the number of captured cancer cells was in a range of 11.7 to 43.8 per 7.5 mL, and as for the gastric cancer patient group, the number of captured cancer cells was in a range of 10.4 to 60.4 per 7.5 mL. A specimen number and a type of cancer, and the number of cancer cells actually isolated and a volume of a whole blood specimen actually injected, were as illustrated in Table 2.

TABLE 2

| Specimen number | Type of cancer | Stage | Number of cancer cells | Volume of whole blood | Number of cancer cells per 7.5 mL |
|---|---|---|---|---|---|
| L58 | Lung cancer | IIA | 5 | 3.2 | 11.7 |
| L59 | Lung cancer | — | 0 | 2.4 | 0 |
| L60 | Lung cancer | IIIB | 0 | 3.6 | 0 |
| L61 | Lung cancer | IV | 0 | 4 | 0 |
| L62 | Lung cancer | IV | 4 | 2.4 | 12.5 |
| L63 | Lung cancer | IIIA | 16 | 4.4 | 27.3 |
| L64 | Lung cancer | IB | — | 4.4 | — |
| L65 | Lung cancer | IB | 5 | 2.2 | 14.0 |
| L66 | Lung cancer | IV | 21 | 3.6 | 43.8 |
| L68 | Lung cancer | IV | 0 | 3 | 0 |

TABLE 2-continued

| Specimen number | Type of cancer | Stage | Number of cancer cells | Volume of whole blood | Number of cancer cells per 7.5 mL |
|---|---|---|---|---|---|
| G110 | Gastric cancer | IIIB | 0 | 3.2 | 0 |
| G111 | Gastric cancer | IIIC | 0 | 4.2 | 0 |
| G113 | Gastric cancer | IIIC | 0 | 4.2 | 0 |
| G115 | Gastric cancer | IA | 15 | 3.2 | 35.2 |
| G118 | Gastric cancer | IIIC | 18 | 4.4 | 30.7 |
| G119 | Gastric cancer | IV | 29 | 3.6 | 60.4 |
| G120 | Gastric cancer | IIIC | 9 | 3.6 | 18.8 |
| G121 | Gastric cancer | IIA | 0 | 3.6 | 0 |
| G122 | Gastric cancer | IIIB | 5 | 3.6 | 10.4 |
| G123 | Gastric cancer | IA | 0 | 3.6 | 0 |
| G124 | Gastric cancer | IIIB | 0 | 4 | 0 |
| G125 | Gastric cancer | — | 0 | 3.4 | 0 |
| G126 | Gastric cancer | IA | 0 | 4.2 | 0 |

Figure 21:
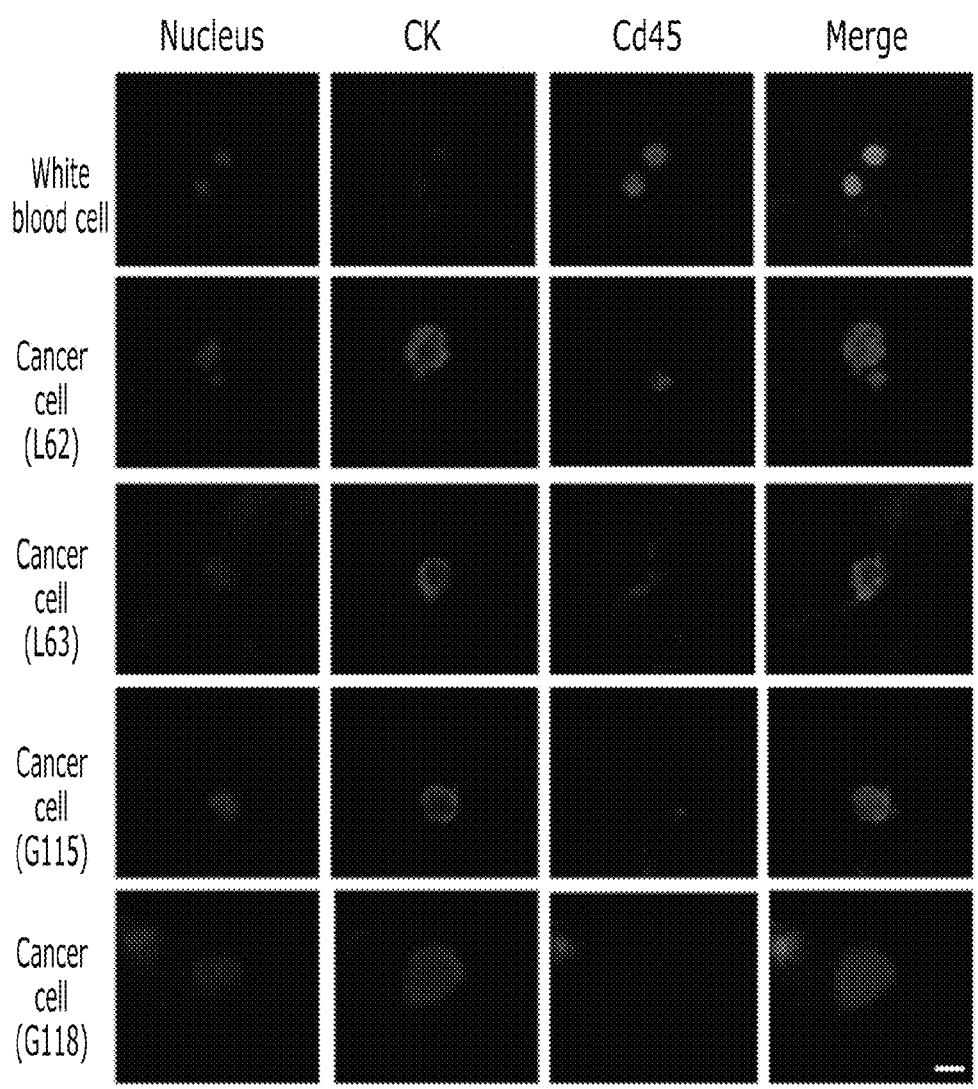
FIG. 21 is a microphotograph illustrating a result of immunofluorescent staining of a white blood cell and cancer cells detected by the rare cell isolation device according to the third exemplary embodiment of the present invention.

FIG. 21 shows microphotographs illustrating a result of immunofluorescent staining of white blood cells and cancer cells detected by the rare cell isolation device according to the third exemplary embodiment of the present invention.

Referring to FIG. 21, it can be seen that a nucleus was present in all of the captured white blood cells and cancer cells (a portion stained blue in FIG. 21), and it can be seen that as for the cancer cells, cytokeratin (CK) was expressed (a portion stained red in FIG. 21). Further, it can be seen that as for the white blood cells, CD45 was expressed.

Figure 22:
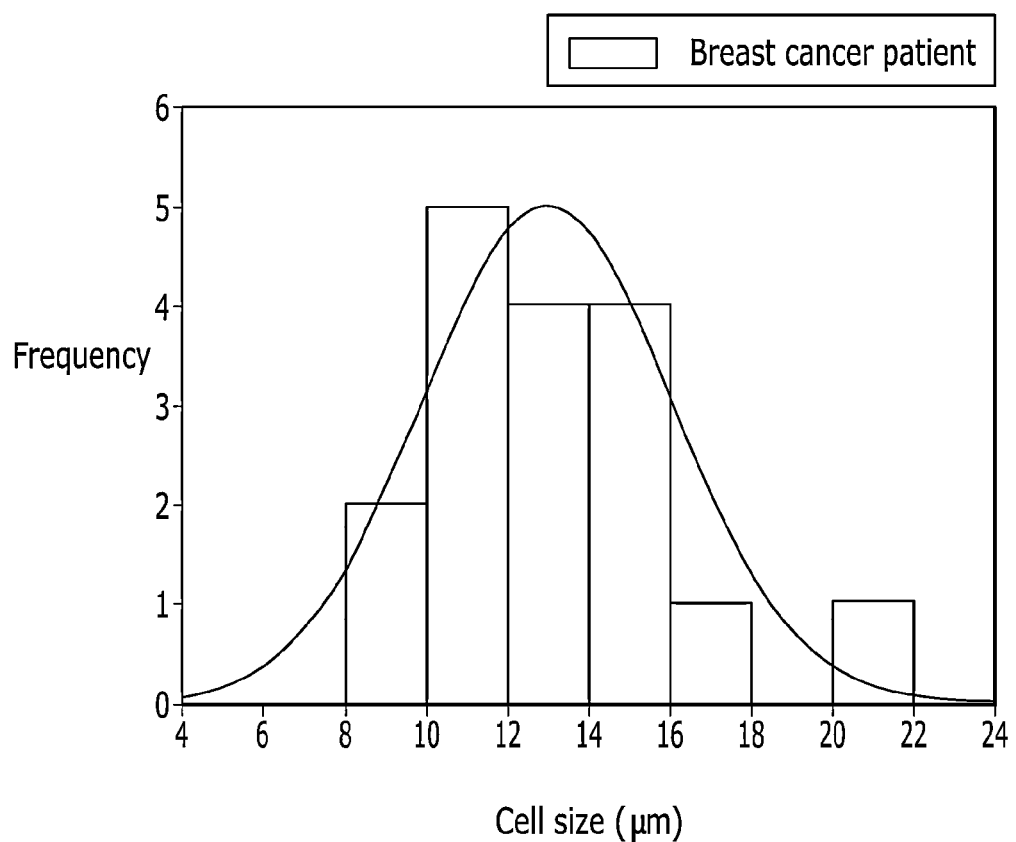
FIG. 22 is a graph illustrating a size distribution of breast cancer cells detected by the rare cell isolation device according to the third exemplary embodiment of the present invention.
Figure 23:
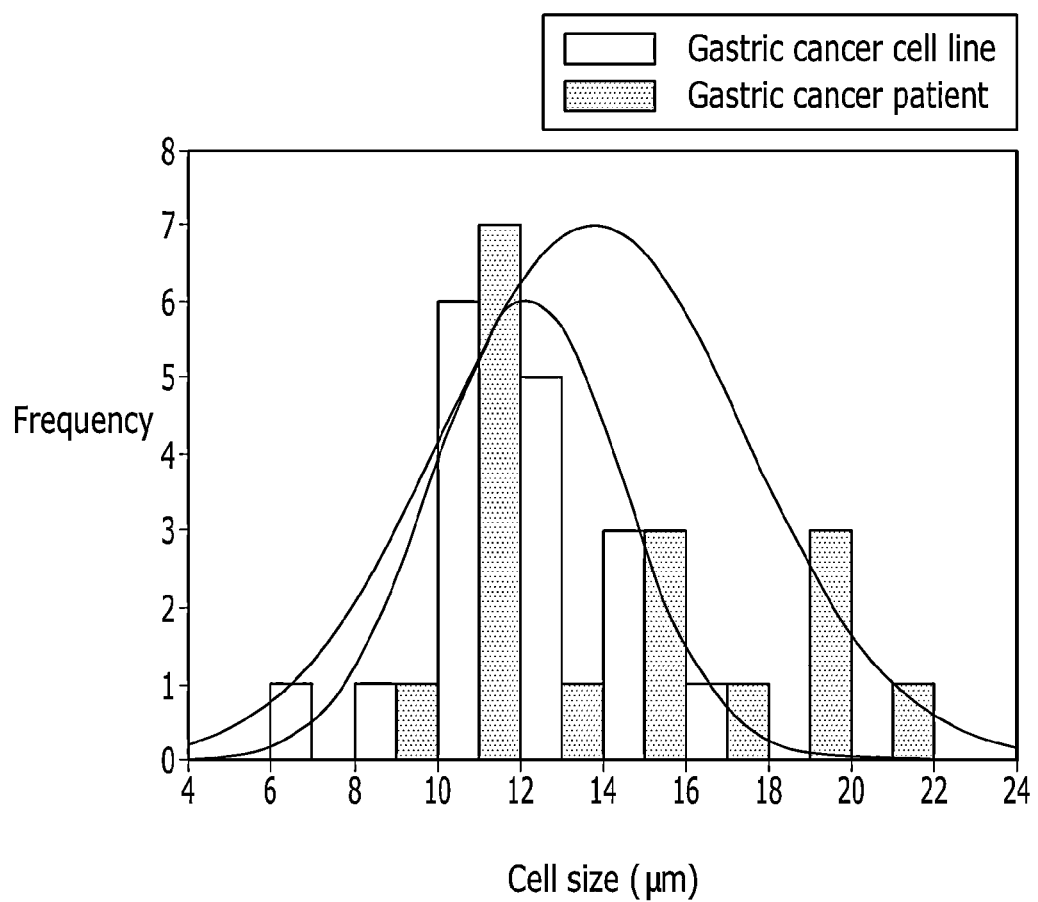
FIG. 23 is a graph comparing a size distribution of gastric cancer cells with a size distribution of gastric cancer cell lines detected by the rare cell isolation device according to the third exemplary embodiment of the present invention.

FIG. 22 is a graph illustrating a size distribution of breast cancer cells detected by the rare cell isolation device according to the third exemplary embodiment of the present invention, and FIG. 23 is a graph comparing a size distribution of gastric cancer cells with a size distribution of gastric cancer cell lines detected by the rare cell isolation device according to the third exemplary embodiment of the present invention.

Referring to FIG. 22 and FIG. 23, it can be seen that the cancer cells captured from the breast cancer patients had sizes in a range of 8 μm to 22 μm, and the cancer cells captured from the gastric cancer patients had sizes in a range of 9 μm to 22 μm.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A cell isolation device comprising:
a filtration membrane which filters a biospecimen;
a first body which is disposed above the filtration membrane and includes a first inlet for injecting the biospecimen,
a second body which is disposed under the first body and bonded to the filtration membrane, and
a filtrate storage unit which is formed at a contact portion between the first body and the second body and is connected to the filtration membrane with a first flow path,
wherein the first body and the second body have a disk-shaped structure to be rotatable around their centers,
wherein an interior of the first flow path is devoid of any filters,
wherein the filtration membrane is disposed to be separated from the center of the second body in a radial direction,
wherein the first body includes:
an upper plate through which the first inlet penetrates;
a first intermediate plate which is coupled to a lower part of the upper plate, on its one side; and
a first guiding unit which is formed at a contact portion between the upper plate and the first intermediate plate and of which one side is connected to the first inlet and the other side is connected to the filtration membrane, and
wherein the second body includes:
a second intermediate plate that is bonded to the filtration membrane; and
a lower plate which is coupled to a lower part of the second intermediate plate
wherein the second intermediate plate includes a penetrating portion formed at a contact portion with the first guiding unit, and
wherein the penetrating portion includes:
a first hole which is formed in a circular shape at the second intermediate plate; and
a second hole which is formed at a lower part of the second intermediate plate and formed in a concentric circular shape having a greater exterior diameter than the first hole.

2. The cell isolation device of claim 1, wherein the upper plate includes a ventilation hole which is connected to the first guiding unit.

3. The cell isolation device of claim 1, wherein the second intermediate plate or the lower plate includes the first flow path which connects the filtration membrane and the filtrate storage unit.

4. The cell isolation device of claim 3, wherein the first inlet is disposed between the center of the first body and the filtration membrane.

5. The cell isolation device of claim 4, wherein the first guiding unit includes:
a first portion which penetrates through the first intermediate plate and gradually increases in width in a radial direction of the first body based the center of the first body; and
a second portion which penetrates through the first intermediate plate and gradually decreases in width in the radial direction of the first body from an end of the first portion based on the center of the first body.

6. The cell isolation device of claim 1, wherein the filtration membrane penetrates through a lower side of the second hole and is bonded to the lower part of the second intermediate plate.

7. The cell isolation device of claim 6, wherein there are multiple first guiding units formed in a radial direction based on a central portion of the body.

8. The cell isolation device of claim 7, wherein the first body includes:
a second inlet which penetrates through the upper plate and is disposed on a central side of the first body; and a second guiding unit which is formed at a contact portion between the upper plate and the first intermediate plate and of which one side is connected to the second inlet and the other side is connected to the second portion.

9. The cell isolation device of claim 8, wherein
there are multiple second inlets and second guiding units disposed in a radial direction based on the center of the first body.

10. The cell isolation device of claim 9, wherein
a detection solution storage unit connected to the filtration membrane is formed at the contact portion between the first body and the second body, and
a second flow path which is branched from the first flow path between the second intermediate plate and the lower plate and connects the first filtration membrane and the detection solution storage unit is formed, and
an interior of the second flow path is devoid of any filters.

11. The cell isolation device of claim 10, wherein
a reversible valve is provided in the first flow path, the second flow path, or at least one of third flow paths which connect the first guiding unit and the second guiding unit to adjust a flow rate flowing into the filtration membrane and a flow rate discharged from the filtration membrane.

12. A cell isolation method using the cell isolation device of claim 1, comprising:
injecting the biospecimen into the cell isolation device;
guiding the biospecimen to the filtration membrane by generating centrifugal force; and
filtering the biospecimen through the filtration membrane.

13. A cell detection method using the cell isolation device of claim 8, comprising:
injecting the biospecimen into the cell isolation device;
guiding the biospecimen to the filtration membrane by generating centrifugal force;
filtering the biospecimen through the filtration membrane;
washing the cell isolated on the filtration membrane;
staining the cell; and
detecting the stained cell.

14. The cell detection method of claim 13, wherein
the step of staining includes injecting a staining reagent into the second guiding unit and staining the cell isolated on the filtration membrane.

15. The cell detection method of claim 14, wherein
the step of detecting includes detecting the stained cell using an optical microscope.

16. The cell detection method for detecting cells isolated by the cell isolation method according to claim 10, comprising:
injecting the biospecimen into the cell isolation device;
guiding the biospecimen to the filtration membrane by generating centrifugal force;
filtering the biospecimen through the filtration membrane;
washing the cell isolated on the filtration membrane;
lysing the cell; and
specifically amplifying a gene of the lysing cell.

17. The cell isolation method of claim 16, wherein
the step of cell lysis includes injecting a cell lysis solution into the second guiding unit and lysing the cell.

* * * * *